US012606526B2

(12) United States Patent
Wang et al.

(10) Patent No.: US 12,606,526 B2
(45) Date of Patent: Apr. 21, 2026

(54) SUBSTITUTED SALICYLAMIDE COMPOUNDS AND USE THEREOF

(71) Applicant: HELIOS HUAMING BIOPHARMA CO., LTD., Suzhou (CN)

(72) Inventors: Yanming Wang, Suzhou (CN); Yan Xia, Suzhou (CN); Zhengwei Guo, Suzhou (CN); Jinquan Sun, Suzhou (CN); Mingde Xia, Suzhou (CN)

( * ) Notice: Subject to any disclaimer, the term of this patent is extended or adjusted under 35 U.S.C. 154(b) by 382 days.

(21) Appl. No.: 18/260,703

(22) PCT Filed: Jan. 10, 2022

(86) PCT No.: PCT/CN2022/070969
§ 371 (c)(1),
(2) Date: Jul. 7, 2023

(87) PCT Pub. No.: WO2022/148457
PCT Pub. Date: Jul. 14, 2022

(65) Prior Publication Data

US 2024/0092737 A1 Mar. 21, 2024

(30) Foreign Application Priority Data

Jan. 11, 2021 (WO) ................ PCT/CN2021/071015

(51) Int. Cl.

| | |
|---|---|
| ***C07D 213/56*** | (2006.01) |
| ***A61K 45/06*** | (2006.01) |
| ***C07C 257/14*** | (2006.01) |
| ***C07D 495/04*** | (2006.01) |

(52) U.S. Cl.
CPC ............ *C07D 213/56* (2013.01); *A61K 45/06* (2013.01); *C07C 257/14* (2013.01); *C07D 495/04* (2013.01)

(58) Field of Classification Search
None
See application file for complete search history.

(56) References Cited

FOREIGN PATENT DOCUMENTS

| | | | |
|---|---|---|---|
| JP | 2002212157 | A | 7/2002 |
| WO | 1997008145 | A1 | 3/1997 |
| WO | 2004113277 | A2 | 12/2004 |
| WO | 2005014533 | A2 | 2/2005 |
| WO | 2005051901 | A1 | 6/2005 |
| WO | 2013148333 | A1 | 10/2013 |
| WO | 2018102006 | A1 | 6/2018 |

OTHER PUBLICATIONS

International Search Report and Written Opinion for International Application No. PCT/CN2022/070969, mailed Apr. 8, 2022.

Glenn et al. "Antiproliferative and Phenotype-Transforming Antitumor Agents Derived from Cysteine" Apr. 29, 2004, J. Med. Chem. 47:2984-2994.

Poshetti et al. "The Intramolecular HB Interactions Evidenced in Dibenzoyl Oxalamide Derivatives: NMR; QTAIM, and NCI Studies" Dec. 8, 2017, J. Phys. Chem. A, 122:199-208, with supporting document (53 pages).

Thuring et al. "Comparative Study of the Active Site Caging of Serine Proteases: Thrombin and Factor Xa" Jan. 18, 2002 Biochemistry 41:2002-2013.

Matsuzawa et al. "Solvent-Dependent Self-Discrimination of Bis(2-hydroxyphenyl)diamides" Apr. 6, 2010 Chem. Eur. J. 16:5036-5042.

Causey et al., "The Development of N-α-(2-Carboxyl)benzoyl-N5-(2-fluoro-1-iminoethyl)-L-ornithine Amide (o-F-amidine) and N-α-(2-Carboxyl)benzoyl-N5-(2-chloro-1-iminoethyl)-L-ornithine Amide (o-Cl-amidine) As Second Generation Protein Arginine Deiminase (PAD) Inhibitors", Journal of Medicinal Chemistry, vol. 54(19), Jan. 1, 2011, pp. 6919-6935.

Extended European Search Report issued by European Patent Office for European Patent Application No. 22736618.4 dated Nov. 8, 2024.

*Primary Examiner* — Samantha L Shterengarts
(74) *Attorney, Agent, or Firm* — DLA Piper LLP (US)

(57) ABSTRACT

Provided is a compound or a pharmaceutically acceptable salt, prodrug, or metabolite thereof, or a solvate or hydrate of any of the foregoing and a use in treatment of a disease or disorder.

46 Claims, No Drawings

SUBSTITUTED SALICYLAMIDE COMPOUNDS AND USE THEREOF

CROSS-REFERENCE TO RELATED APPLICATIONS

This application is a National Stage entry of International Application No. PCT/CN2022/070969 filed Jan. 10, 2022, which claims the benefit of International Application No. PCT/CN2021/071015 filed Jan. 11, 2021, each of which are hereby incorporated by reference in its entirety.

BACKGROUND OF THE INVENTION

Peptidyl arginine deiminase (PAD) citrullinates arginine (Arg) and mono-methyl Arg residues in substrate proteins such as transcription factors and histones. PAD affects diseases via its role in cancer, immune responses and other cellular events. There is a continuing need for PAD inhibitors in the treatment of diseases.

SUMMARY OF THE INVENTION

The present disclosure provides a compound or a pharmaceutically acceptable salt or solvate thereof and use thereof, which is used as a PAD inhibitor. The compound, pharmaceutically acceptable salt or solvate thereof is used for treating a disease or disorder. The compound or the present disclosure reveals effect in PAD4 inhibition.

In one aspect, the present application provides a compound of formula (I):

(I)

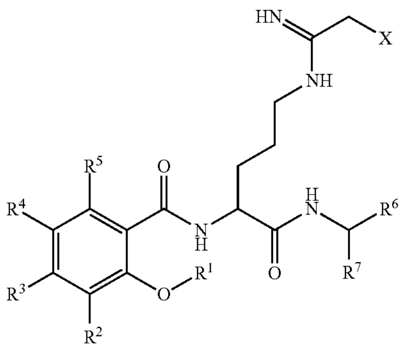

or a pharmaceutically acceptable salt, prodrug, or metabolite thereof, or a solvate or hydrate of any of the foregoing, wherein, X is halogen; $R^1$ is selected from the group consisting of optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl; each of $R^2$, $R^3$, $R^4$ and $R^5$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, or $R^2$ and $R^3$ combined with the atoms to which they are attached form an optionally substituted ring A1, said ring A1 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A1 is unsubstituted or independently substituted with one or more $R^{9a}$;

or $R^3$ and $R^4$ combined with the atoms to which they are attached form an optionally substituted ring A2, said ring A2 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A2 is unsubstituted or independently substituted with one or more $R^{9b}$;

or $R^4$ and $R^5$ combined with the atoms to which they are attached form an optionally substituted ring A3, said ring A3 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A3 is unsubstituted or independently substituted with one or more $R^{9c}$;

each of $R^6$ and $R^7$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, each of $R^{9a}$, $R^{9b}$ and $R^{9c}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

In some embodiments, wherein X is selected from the group consisting of F and Cl.

In some embodiments, wherein $R^1$ is optionally substituted ($C_1$-$C_8$) alkyl.

In some embodiments, wherein $R^1$ is optionally substituted methyl.

In some embodiments, wherein $R^2$ is hydrogen.

In some embodiments, wherein $R^3$ is hydrogen.

In some embodiments, wherein $R^4$ is selected from the group consisting of hydrogen, halogen, and optionally substituted ($C_6$-$C_{10}$) aryl.

In some embodiments, wherein $R^4$ is selected from the group consisting of F and Cl.

In some embodiments, wherein $R^4$ is optionally substituted phenyl.

In some embodiments, wherein $R^4$ is substituted with one or more $R^8$, each $R^8$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$)

heteroaryl, optionally substituted ($C_1$-$C_8$) alkoxy and optionally substituted ($C_1$-$C_8$) alkylamino.

In some embodiments, wherein $R^8$ is selected from the group consisting of hydrogen, halogen, and optionally substituted ($C_1$-$C_8$) alkyl.

In some embodiments, wherein $R^8$ is selected from the group consisting of F and Cl.

In some embodiments, wherein $R^8$ is optionally substituted methyl.

In some embodiments, wherein $R^2$ and $R^3$ combined with the atoms to which they are attached form an optionally substituted ring A1, said ring A1 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

In some embodiments, wherein ring A1 is optionally substituted ($C_6$-$C_{10}$) aryl.

In some embodiments, wherein ring A1 is optionally substituted phenyl.

In some embodiments, wherein ring A1 is substituted with one or more $R^{9a}$, each $R^{9a}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

In some embodiments, wherein $R^{9a}$ is selected from the group consisting of hydrogen, optionally substituted ($C_1$-$C_8$) alkoxy, and optionally substituted ($C_1$-$C_8$) alkylamino.

In some embodiments, wherein $R^{9a}$ is optionally substituted N,N-dimethylamino.

In some embodiments, wherein $R^3$ and $R^4$ combined with the atoms to which they are attached form an optionally substituted ring A2, said ring A2 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

In some embodiments, wherein ring A2 is optionally substituted ($C_6$-$C_{10}$) aryl.

In some embodiments, wherein ring A2 is optionally substituted phenyl.

In some embodiments, wherein ring A2 is substituted with one or more $R^{9b}$, each $R^{9b}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

In some embodiments, wherein $R^{9b}$ is selected from the group consisting of hydrogen, optionally substituted ($C_1$-$C_8$) alkoxy, and optionally substituted ($C_1$-$C_8$) alkylamino.

In some embodiments, wherein $R^{9b}$ is optionally substituted methoxy.

In some embodiments, wherein $R^5$ is selected from the group consisting of hydrogen, halogen, and optionally substituted ($C_1$-$C_8$) alkoxy.

In some embodiments, wherein $R^5$ is selected from the group consisting of hydrogen, halogen, and optionally substituted methoxy.

In some embodiments, wherein $R^5$ is selected from the group consisting of F and Cl.

In some embodiments, wherein $R^5$ is optionally substituted methoxy.

In some embodiments, wherein at least one of $R^6$ and $R^7$ is not hydrogen.

In some embodiments, wherein $R^6$ is selected from the group consisting of optionally substituted ($C_6$-$C_{10}$) aryl, and optionally substituted ($C_1$-$C_9$) heteroaryl.

In some embodiments, wherein $R^6$ is optionally substituted phenyl.

In some embodiments, wherein $R^6$ is optionally substituted pyridyl.

In some embodiments, wherein $R^6$ is substituted with one or more $R^{10}$, each $R^{10}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy, optionally substituted ($C_1$-$C_8$) alkylamino and optionally substituted group

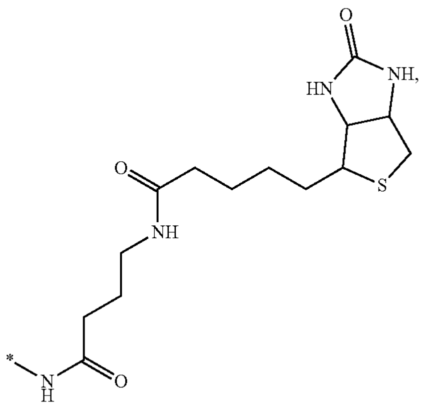 [SMILES: *NC(=O)CCCNC(=O)CCCCC1SCC2NC(=O)NC21]

wherein the asterisk "*" in the structure formulas indicates the available radical ends to be connected.

In some embodiments, wherein $R^6$ is substituted with one or more $R^{10}$, each $R^{10}$ is independently selected from the group consisting of hydrogen, halogen, optionally substituted ($C_1$-$C_8$) alkyl, optionally substituted ($C_1$-$C_8$) alkoxy and optionally substituted group

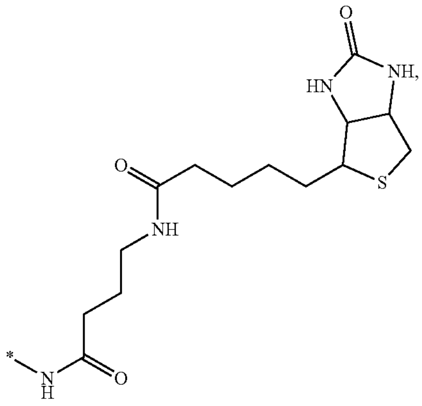 [SMILES: *NC(=O)CCCNC(=O)CCCCC1SCC2NC(=O)NC21]

wherein the asterisk "*" in the structure formulas indicates the available radical ends to be connected.

In some embodiments, wherein $R^{10}$ is selected from the group consisting of F and Cl.

In some embodiments, wherein $R^{10}$ is optionally substituted methyl.

In some embodiments, wherein $R^{10}$ is optionally substituted methoxy.

In some embodiments, wherein $R^{10}$ is optionally substituted group

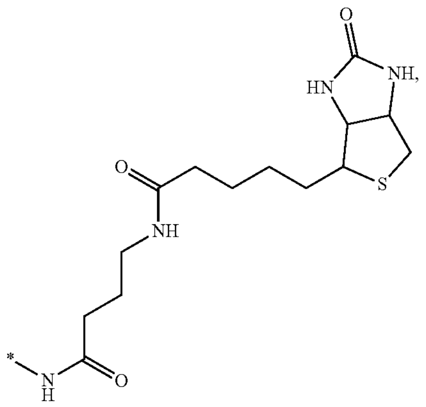 [SMILES: *NC(=O)CCCNC(=O)CCCCC1SCC2NC(=O)NC21]

wherein the asterisk "*" in the structure formulas indicates the available radical ends to be connected.

In another aspect, the present application provides a compound of formula (II):

(II)

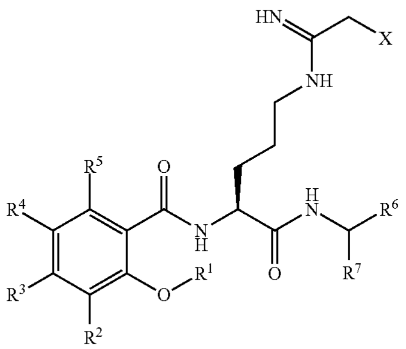

or a pharmaceutically acceptable salt, prodrug, or metabolite thereof, or a solvate or hydrate of any of the foregoing, wherein, X is halogen; $R^1$ is selected from the group consisting of optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl; each of $R^2$, $R^3$, $R^4$ and $R^5$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, or $R^2$ and $R^3$ combined with the atoms to which they are attached form an optionally substituted ring A1, said ring A1 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A1 is unsubstituted or independently substituted with one or more $R^{9a}$;

or $R^3$ and $R^4$ combined with the atoms to which they are attached form an optionally substituted ring A2, said ring A2 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A2 is unsubstituted or independently substituted with one or more $R^{9b}$;

or $R^4$ and $R^5$ combined with the atoms to which they are attached form an optionally substituted ring A3, said ring A3 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A3 is unsubstituted or independently substituted with one or more $R^{9c}$;

each of $R^6$ and $R^7$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, each of $R^{9a}$, $R^{9b}$ and $R^{9c}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

In some embodiments, wherein X is selected from the group consisting of F and Cl.

In some embodiments, wherein $R^1$ is optionally substituted ($C_1$-$C_8$) alkyl.

In some embodiments, wherein $R^1$ is optionally substituted methyl.

In some embodiments, wherein $R^2$ is hydrogen.

In some embodiments, wherein $R^3$ is hydrogen.

In some embodiments, wherein $R^4$ is selected from the group consisting of hydrogen, halogen, and optionally substituted ($C_6$-$C_{10}$) aryl.

In some embodiments, wherein $R^4$ is selected from the group consisting of F and Cl.

In some embodiments, wherein $R^4$ is optionally substituted phenyl.

In some embodiments, wherein $R^4$ is substituted with one or more $R^8$, each $R^8$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally ally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

In some embodiments, wherein each $R^8$ is selected from the group consisting of hydrogen, halogen, and optionally substituted ($C_1$-$C_8$) alkyl.

In some embodiments, wherein each $R^8$ is selected from the group consisting of F and Cl.

In some embodiments, wherein each $R^8$ is optionally substituted methyl.

In some embodiments, wherein $R^2$ and $R^3$ combined with the atoms to which they are attached form an optionally substituted ring A1, said ring A1 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

In some embodiments, wherein ring A1 is optionally substituted ($C_6$-$C_{10}$) aryl.

In some embodiments, wherein ring A1 is optionally substituted phenyl.

In some embodiments, wherein ring A1 is substituted with one or more $R^{9a}$, each $R^{9a}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

In some embodiments, wherein each $R^{9a}$ is selected from the group consisting of hydrogen, optionally substituted ($C_1$-$C_8$) alkoxy, and optionally substituted ($C_1$-$C_8$) alkylamino.

In some embodiments, wherein each $R^{9a}$ is optionally substituted N,N-dimethylamino.

In some embodiments, wherein $R^3$ and $R^4$ combined with the atoms to which they are attached form an optionally substituted ring A2, said ring A2 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

In some embodiments, wherein ring A2 is optionally substituted ($C_6$-$C_{10}$) aryl.

In some embodiments, wherein ring A2 is optionally substituted phenyl.

In some embodiments, wherein ring A2 is substituted with one or more $R^{9b}$, each $R^{9b}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

In some embodiments, wherein each $R^{9b}$ is selected from the group consisting of hydrogen, optionally substituted ($C_1$-$C_8$) alkoxy, and optionally substituted ($C_1$-$C_8$) alkylamino.

In some embodiments, wherein each $R^{9b}$ is optionally substituted methoxy.

In some embodiments, wherein $R^5$ is selected from the group consisting of hydrogen, halogen, and optionally substituted ($C_1$-$C_8$) alkoxy.

In some embodiments, wherein $R^5$ is selected from the group consisting of hydrogen, halogen, and optionally substituted methoxy.

In some embodiments, wherein $R^5$ is selected from the group consisting of F and Cl.

In some embodiments, wherein $R^5$ is optionally substituted methoxy.

In some embodiments, wherein at least one of $R^6$ and $R^7$ is not hydrogen.

In some embodiments, wherein $R^6$ is selected from the group consisting of optionally substituted ($C_6$-$C_{10}$) aryl, and optionally substituted ($C_1$-$C_9$) heteroaryl.

In some embodiments, wherein $R^6$ is optionally substituted phenyl.

In some embodiments, wherein $R^6$ is optionally substituted pyridyl.

In some embodiments, wherein $R^6$ is substituted with one or more $R^{10}$, each $R^{10}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy, optionally substituted ($C_1$-$C_8$) alkylamino and optionally substituted group

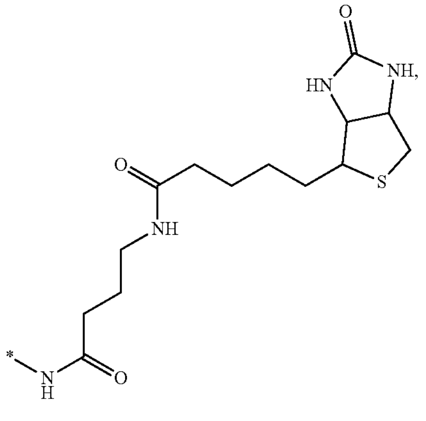 [SMILES: *NC(=O)CCCNC(=O)CCCCC1SCC2NC(=O)NC21]

wherein the asterisk "*" in the structure formulas indicates the available radical ends to be connected.

In some embodiments, wherein $R^6$ is substituted with one or more $R^{10}$, each $R^{10}$ is independently selected from the group consisting of hydrogen, halogen, optionally substituted ($C_1$-$C_8$) alkyl, optionally substituted ($C_1$-$C_8$) alkoxy and optionally substituted group

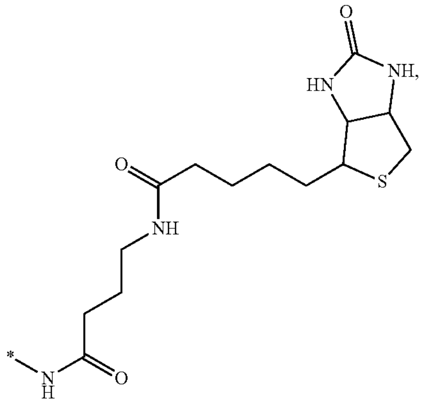 [SMILES: *NC(=O)CCCNC(=O)CCCCC1SCC2NC(=O)NC21]

wherein the asterisk "*" in the structure formulas indicates the available radical ends to be connected.

In some embodiments, wherein each $R^{10}$ is selected from the group consisting of F and Cl.

In some embodiments, wherein each $R^{10}$ is optionally substituted methyl.

In some embodiments, wherein each $R^{10}$ is optionally substituted methoxy.

In some embodiments, wherein each $R^{10}$ is optionally substituted group

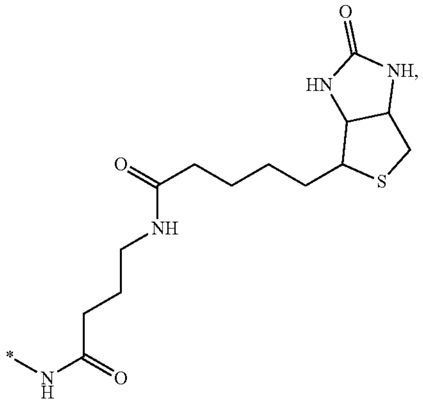 [SMILES: *NC(=O)CCCNC(=O)CCCCC1SCC2NC(=O)NC21]

wherein the asterisk "*" in the structure formulas indicates the available radical ends to be connected.

In another aspect, the present application provides a compound or a pharmaceutically acceptable salt, prodrug, or metabolite thereof, or a solvate or hydrate of any of the foregoing, wherein, said compound is selected from the group consisting of:

EX-1

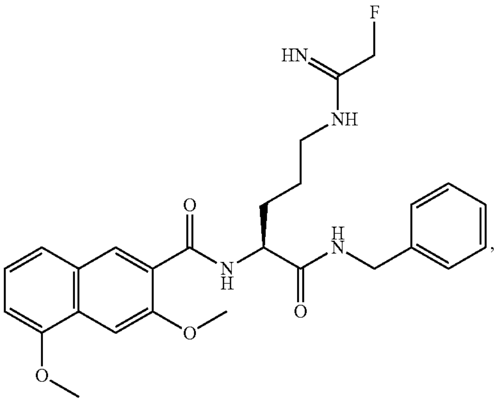

EX-2

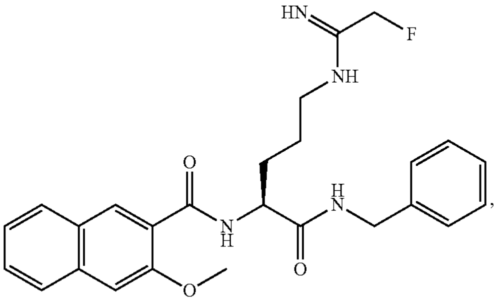

EX-3

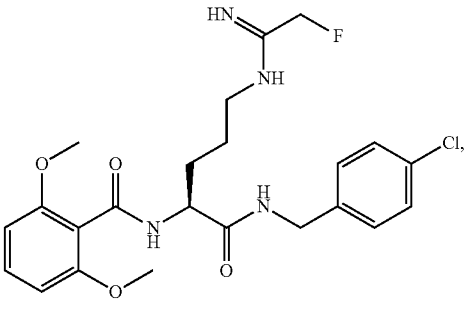

EX-4

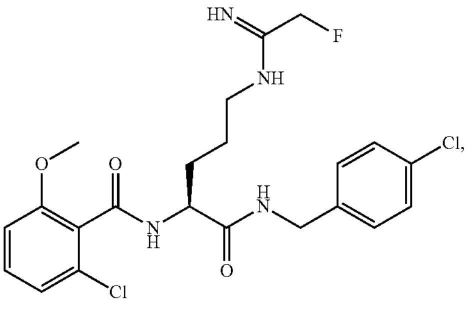

-continued
EX-5
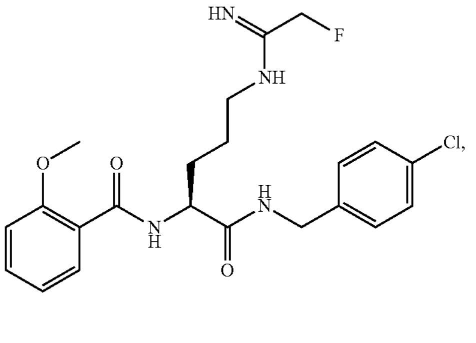
EX-6
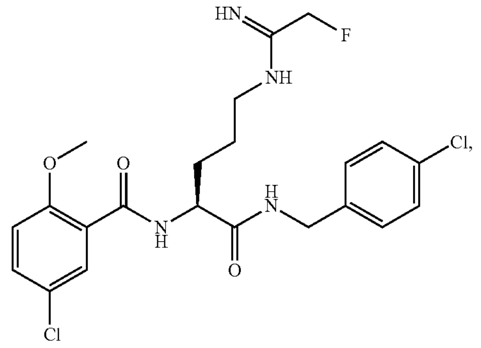
EX-7
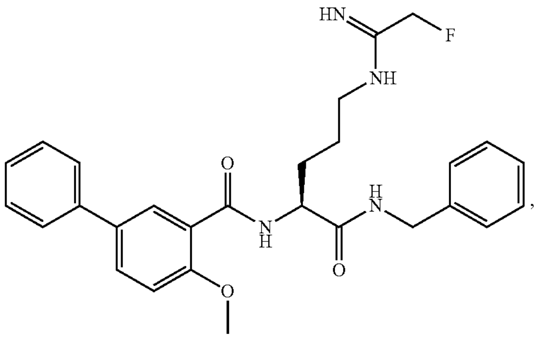
EX-8
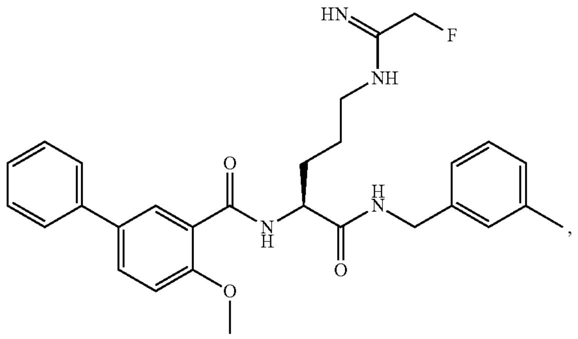
EX-9
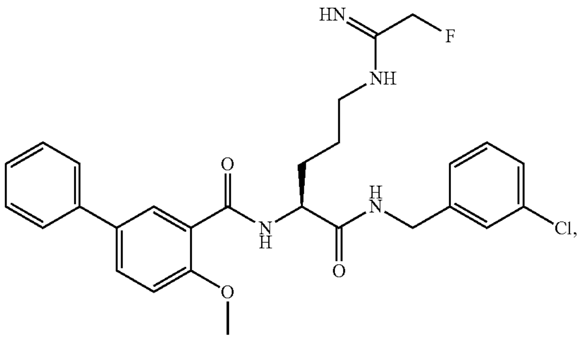
EX-10
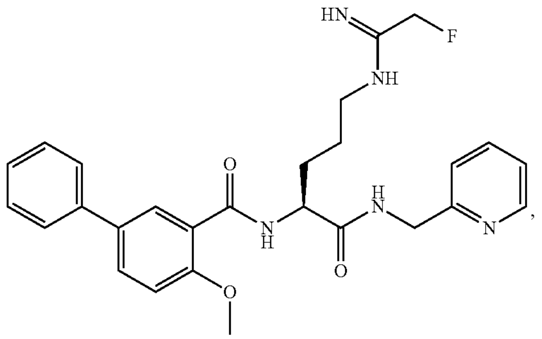
EX-11
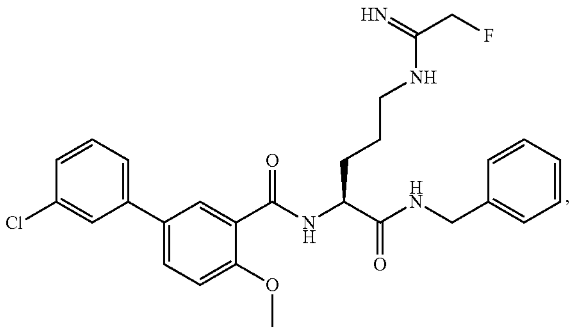
EX-12
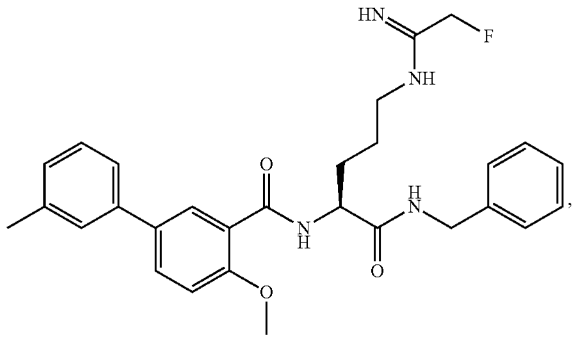

-continued
EX-13
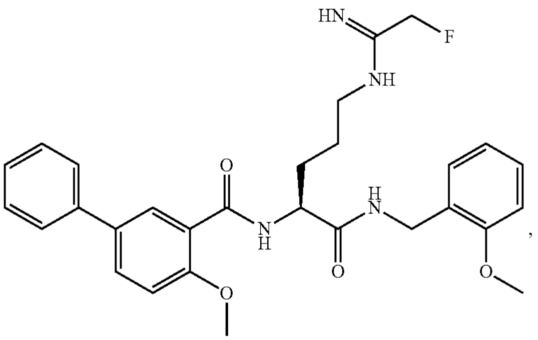
,
EX-14
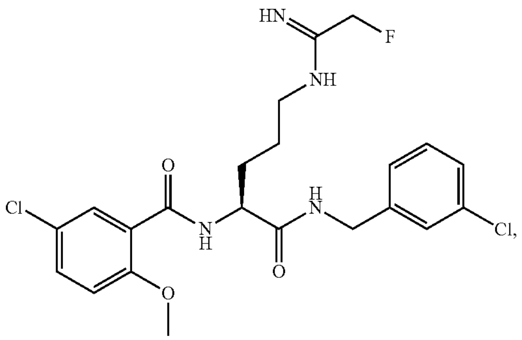
EX-15
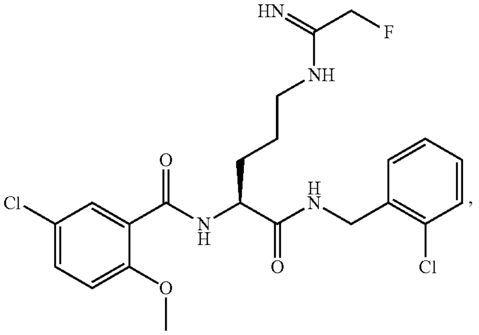
,
EX-16
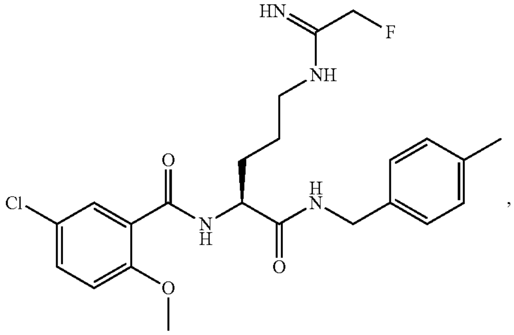
,
EX-17
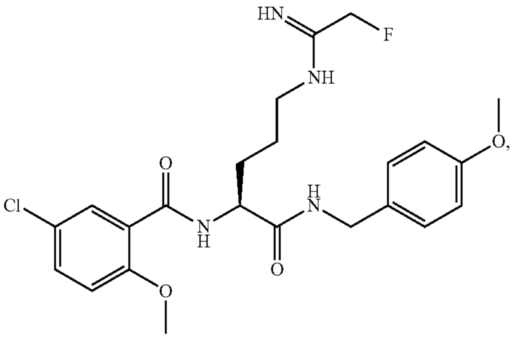
EX-18
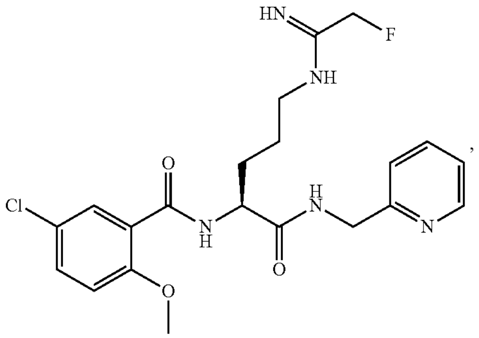
,
EX-19
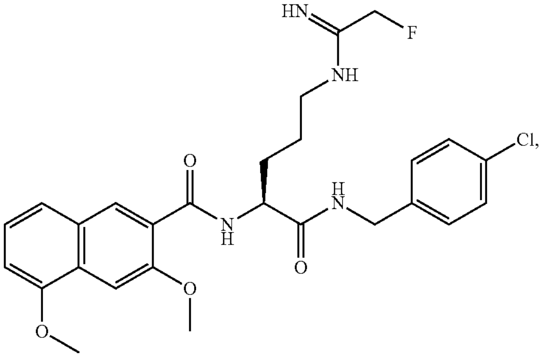
EX-20
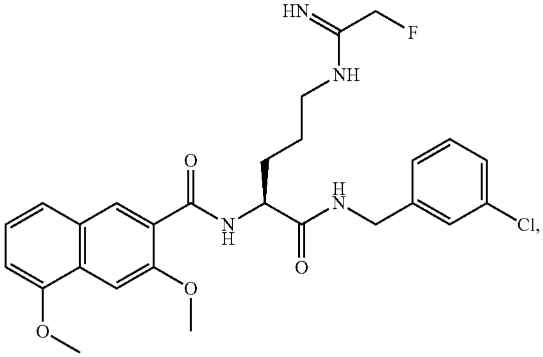

-continued

EX-21

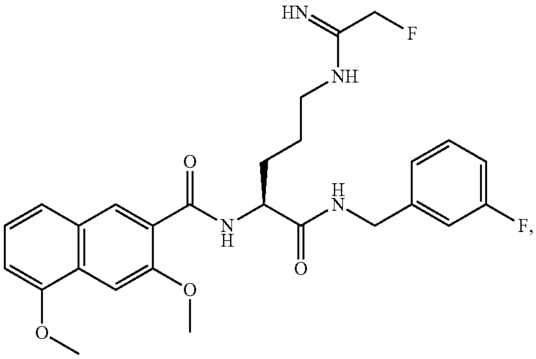

,

EX-22

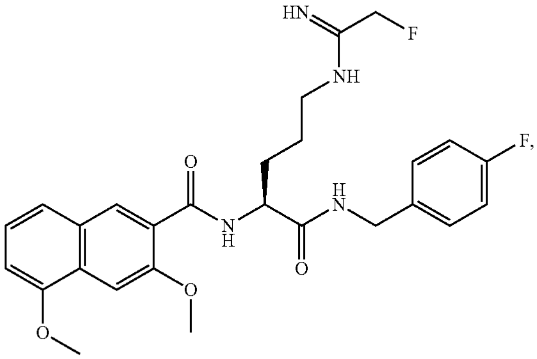

,

EX-23

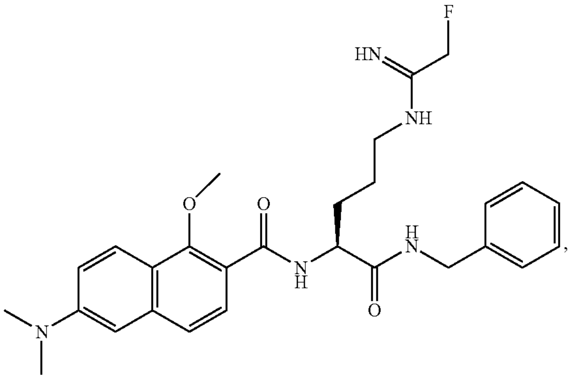

, and

EX-24

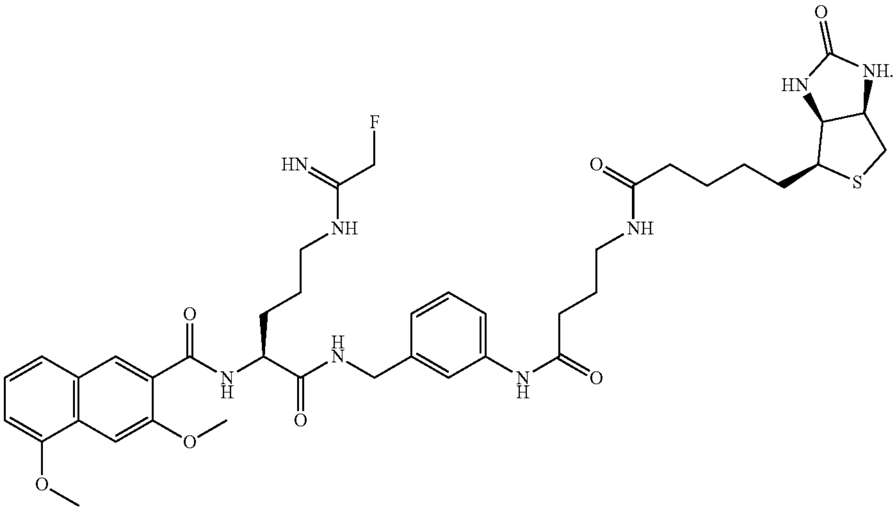

.

In another aspect, the present application provides a composition comprising a compound of any of the present application or a pharmaceutically acceptable salt, prodrug, or metabolite thereof, or a solvate or hydrate of any of the foregoing, and optionally a pharmaceutically acceptable carrier.

In some embodiments, wherein said pharmaceutically acceptable salt is a hydrochloride salt.

In some embodiments, wherein said composition comprises an effective amount of a compound of any of the present application, or a pharmaceutically acceptable salt, prodrug, or metabolite thereof, or a solvate or hydrate of any of the foregoing.

In some embodiments, wherein said composition is suitable for parenteral, transdermal, mucosal, nasal, buccal, sublingual, or oral administration to a subject in need thereof.

In another aspect, the present application provides a use of a compound of any of the present application, or a pharmaceutically acceptable salt, prodrug, or metabolite thereof, or a solvate or hydrate of any of the foregoing, in the preparation of a PAD inhibitor.

In some embodiments, wherein said PAD inhibitor is selected from the group consisting of a PAD2 inhibitor and a PAD4 inhibitor.

In some embodiments, wherein said PAD inhibitor is a PAD4 inhibitor.

In some embodiments, wherein said PAD inhibitor attenuates an activity of a protein arginine deiminase (PAD).

In some embodiments, wherein said PAD is selected from the group consisting of PAD2 and PAD4.

In some embodiments, wherein said PAD is PAD4.

In some embodiments, wherein said activity is revealed by an effect on the formation of neutrophil extracellular traps (NETs).

In another aspect, the present application provides a method for preventing and/or treating a disease or disorder, said method comprising administering to a subject in need thereof an effective amount of the compound of the present application, or a pharmaceutically acceptable salt, prodrug, or metabolite thereof, or a solvate or hydrate of any of the foregoing.

In some embodiments, wherein said disease or disorder is selected from the group consisting of neoplastic disease and autoimmune disease.

In some embodiments, wherein said disease or disorder is selected from the group consisting of solid tumor and blood tumor.

In some embodiments, wherein said disease or disorder is selected from the group consisting of lung cancer, blood cancer, breast cancer with or without lung metastasis, colon cancer with or without liver metastasis, rheumatoid arthritis, ischemia-reperfusion injury, and immune response induced during transplant rejection.

In some embodiments, further comprises administering to a subject in need thereof one or more additional therapeutics including radiotherapy, chemotherapy, cell therapy and pharmaceutically active agents.

In some embodiments, said agent is a checkpoint inhibitor.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "halogen", as used herein, generally refers to chloro (Cl), iodo (I), fluoro (F) and bromo (Br). For example, "halogen" groups may be fluoro, chloro, bromo, iodo or the like.

The term "hydroxyalkyl", as used herein, generally refers to an alkyl group of from 1 to 8 carbon atoms substituted with one or more hydroxy groups, wherein the alkyl group is as defined herein. Some non-limiting examples may comprise hydroxyethyl, 2-hydroxypropyl, hydroxymethyl or the like.

The term "alkyl", as used herein, generally refers to a hydrocarbon radical of from 1 to 8 carbon atoms which can be linear or branched, with single or multiple branching. For example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl, 1-hexy, 1-heptyl, 1-octyl or the like. In some instances, the number of carbon atoms in a hydrocarbyl substituent (i.e., alkyl, alkenyl, cycloalkyl, aryl, etc.) may be indicated by the prefix "$C_a$-$C_b$" wherein a is the minimum and b is the maximum number of carbon atoms in the substituent. Thus, for example, "$C_1$-$C_6$ alkyl" may refer to an alkyl substituent containing from 1 to 6 carbon atoms. The "alkyl" groups may be optionally substituted with one or more substitutions.

The term "alkenyl", as used herein, generally refers to a monovalent linear or branched saturated hydrocarbon group of from 2 to 8 carbon atoms, and comprising one, two or three double bonds. For example, ($C_2$-$C_8$) alkenyl may comprise ethenyl, 1-propenyl, 2-propenyl (allyl), iso-propenyl, 2-methyl-I -propenyl, 1-butenyl, 2-butenyl or the like. The "alkenyl" groups may be optionally substituted with one or more substitutions.

The term "alkynyl", as used herein, generally refers to a monovalent linear or branched saturated hydrocarbon group of from 2 to 8 carbon atoms, and comprising one or two triple bonds. For example, ($C_2$-$C_8$) alkynyl may comprise ethynyl, 1-propynyl, 2-propynyl, 1-butynyl, 2-butynyl, 3-butynyl or the like. The "alkynyl" groups may be optionally substituted with one or more substitutions.

The term "haloalkyl", as used herein, generally refers to an alkyl radical of from 1 to 8 carbon atoms having the meaning as defined above wherein one or more hydrogens are replaced with a halogen. For example, monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. For example, haloalkyl radicals may comprise fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl, dichloropropyl or the like. The "haloalkyl" groups may be optionally substituted with one or more substitutions.

As used herein, the term "carbocycle", either alone or within other terms, generally refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles may have 3 to 6 ring atoms, or 5 to 6 ring atoms. Bicyclic carbocycles may have 7 to 12 ring atoms, e.g., arranged as a bicyclo[4,5], [5,5], [5,6] or [6,6] system, or 9 or 10 ring atoms arranged as a bicyclo[5,6] or [6,6] system. The term "carbocycle" may contain, for example, a monocyclic carbocycle ring fused to an aryl ring (e.g., a monocyclic carbocycle ring fused to a benzene ring). Carbocyles may have 3 to 8 carbon ring atoms. In some instances, the number of carbon atoms may be indicated by the prefix "$C_a$-$C_b$" wherein a is the minimum and b is the maximum number of carbon atoms in the substituent. The "carbocycle" groups may be optionally substituted with one or more substitutions. For example, carbocycle may be cycloalkyl. The term "cycloalkyl", as used herein, generally refers to a monovalent saturated monocyclic or bicyclic hydrocarbon group of 3 to 10 carbon atoms, for example, a monovalent saturated monocyclic hydrocarbon group of 3 to 10 carbon atoms. Bicyclic means consisting of two saturated carbocycles having two carbon atoms in common, i.e. the bridge separating the two rings is either a single bond or a chain of one or two carbon atoms. Examples may be cyclopropyl, cyclobutanyl, cyclopentyl, cyclohexyl, cycloheptyl, cyclooctyl, cyclononyl, and cyclodecyl. For example, bicyclic cycloalkyl may be bicyclo[2.2.1]heptanyl, bicyclo[2.2.2]octanyl, adamantanyl or the like.

As used herein, the term "heterocycle", either alone or within other terms, generally refers to a monocyclic, bicyclic, or polycyclic ring system having from 3 to 14 ring atoms (also referred to as ring members) wherein at least one ring atom in at least one ring may be a heteroatom selected from N, O, P, or S (and all combinations and subcombinations of ranges and specific numbers of carbon atoms and heteroatoms therein). The heterocycle may have from 1 to 4 ring heteroatoms independently selected from N, O, P, or S. One or more N, C, or S atoms in a heterocycle may be oxidized. A monocylic heterocycle may have 3 to 7 ring members (e.g., 2 to 6 carbon atoms and 1 to 3 heteroatoms independently selected from N, O, P, or S), and a bicyclic heterocycle may have 5 to 10 ring members (e.g., 4 to 9 carbon atoms and 1 to 3 heteroatoms independently selected from N, O, P, or S). The heterocycle that contains the heteroatom may be non-aromatic. Unless otherwise noted, the heterocycle is attached to its pendant group at any heteroatom or carbon atom that results in a stable structure. In some instances, the number of carbon atoms may be indicated by the prefix "$C_a$-$C_b$" wherein a is the minimum and b is the maximum number of carbon atoms in the substituent. The "heterocycle" groups may be optionally substituted with one or more substitutions. For example, heterocycle may be heterocycloalkyl.

As used herein, the term "aryl", either alone or within other terms, generally refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" may also contain substituents such as phenyl, naphthyl and anthracenyl that are fused to a $C_4$-$C_{10}$ carbocyclic ring, such as a $C_5$ or a $C_6$ carbocyclic ring, or to a 4- to 10-membered heterocyclic ring, wherein a group having such a fused aryl group as a substituent is bound to an aromatic carbon of the aryl group. When such a fused aryl group is substituted with one more substituent, the one or more substituents, unless otherwise specified, may be each bound to an aromatic carbon of the fused aryl group. The fused $C_4$-$C_{10}$ carbocyclic or 4- to 10-membered heterocyclic ring may optionally be optionally substituted. Examples of aryl groups may include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl. In some instances, the number of carbon atoms may be indicated by the prefix "$C_a$-$C_b$" wherein a is the minimum and b is the maximum number of carbon atoms in the substituent. The "aryl" groups may be optionally substituted with one or more substitutions.

As used herein, the term "heteroaryl", either alone or within other terms, generally refers to an aromatic ring structure containing from 5 to 14 ring atoms in which at least one of the ring atoms is a heteroatom (for example, oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents may include but not limited to: 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1, 2, 4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused ring substituents such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. In some instances, the number of carbon atoms may be indicated by the prefix "$C_a$-$C_b$" wherein a is the minimum and b is the maximum number of carbon atoms in the substituent. The "heteroaryl" groups may be optionally substituted with one or more substitutions.

The terms "oxy" or "oxa", as used herein, generally refers to —O—.

The term "alkyloxy" or "alkoxy", as used herein, generally refers to an alkylether substituent, i.e., —O-alkyl. For example, such a substituent may comprise methoxy (—O—$CH_3$), ethoxy, n-propoxy, isopropoxy, n-butoxy, iso-butoxy, sec-butoxy, tert-butoxy, n-pentyloxy, n-hexyloxy, n-heptyloxy, n-octyloxy or the like. The "alkoxy" groups may be optionally substituted with one or more substitutions.

The term "alkylamino", as used herein, generally refers to amino groups which have been substituted with one or two alkyl radicals of 1 to 8 carbon atoms. For example, "alkylamino" groups may be mono- or dialkylated, forming groups such as, for example, N-methylamino, N-ethylamino, N,N-dimethylamino, N,N-diethylamino or the like. For example, methylamino, ethylamino, n-propylamino, isopropylamino, n-butylamino, isobutylamino, sec-butylamino, tert-butylamino, n-pentylamino, n-hexylamino or the like. The "alkylamino" groups may be optionally substituted with one or more substitutions.

The term "aromatic", as used herein, generally refers to the conventional idea of aromaticity as defined in the literature, for example, in IUPAC—Compendium of Chemical Terminology, 2nd, A. D. McNaught & A. Wilkinson (Eds). Blackwell Scientific Publications, Oxford (1997).

The term "optionally substituted", as used herein, generally refers to the anteceding group may be substituted or unsubstituted. When substituted, the hydrogen atoms bound to the carbon, nitrogen, sulfur, or oxygen atoms may be replaced by one or more, for example, 1, 2, 3, or 4, "substituents" which may comprise H, protium, deuterium, tritium, halogen, an alkyl group, an aryl group, a heteroaryl group, an alkyloxy group and an alkylamino group.

The term "independently selected", as used herein, generally refers to each substituent is selected independent of the other(s). Each substituent therefore may be identical to or different from the other substituent(s).

The term "pharmaceutically acceptable", as used herein, generally refers to those compounds, materials, compositions, carriers, and/or dosage forms which are, within the scope of sound medical judgment, suitable for use in contact with the tissues of human beings and animals. In addition, the compounds, material, compositions, carriers, and/or dosage forms may have no excessive toxicity, irritation, allergic response, or other problem or complication, commensurate with a reasonable benefit/risk ratio.

The term "pharmaceutically acceptable salt", as used herein, generally refers to those modified parent compound which are within the scope of sound medical judgment, suitable for use in contact with the tissues of human beings and animals. For example, the parent compound could be modified by making acid or base salts thereof.

Pharmaceutically acceptable salts may include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

The term "solvate", as used herein, generally refers to solvent addition forms that contain either stoichiometric or non stoichiometric amounts of solvent. Some compounds or salts have a tendency to trap a fixed molar ratio of solvent molecules in the crystalline solid state, thus forming a solvate. For example, if the solvent is water, the solvate formed is a hydrate, and if the solvent is alcohol, the solvate formed is an alcoholate. For example, hydrates are formed by the combination of one or more molecules of water with one molecule of the substance in which the water retains its molecular state as $H_2O$.

The term "substituted", as used herein, generally refers to that any one or more atoms on the designated atom is replaced with a selection from the indicated group. In some embodiments, the designated atom's normal valency is not exceeded, and that the substitution results in a stable compound.

The term "pharmaceutically acceptable carrier" as used herein, generally refers to any preparation or supported media that can deliver effective amount of active substance of the disclosure. In addition, the preparation or supported media may don't interfere biological activity of active substance and is non-toxic to hosts or patients. For example, pharmaceutically acceptable carriers may include water, oil, vegetable oil and mineral, cream base, lotion base, ointment base and the like. Additional component may include suspending agent, tackifier and penetration enhancer and the like. Their preparations are known to technicians in cosmetic and topical medication fields.

The term "effective amount", as used herein, generally refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

The term "PAD" or "peptidylarginine deiminase", as used herein, generally refers to the human peptidylarginine deiminase (PAD) family consists of five proteins, including PAD1, PAD2, PAD3, PAD4, and PAD6. For example, PAD4 has a nuclear localization signal and is nuclear localized among PAD family members. PAD family members express in specific tissues. For example, PAD4 is expressed in bone marrow and myeloid lineage cells, such as neutrophils, monocytes and macrophages. PAD4 regulates a unique type of cell death termed NETOSIS wherein neutrophils release chromatin to form neutrophil extracellular traps (NETs). NETs are composed of nuclear chromatin associated with antibacterial proteins such as neutrophil elastase and myeloperoxidase. For example, Both PAD4 and PAD4-mediated protein citrullination can produce self-reacting antibodies under autoimmune conditions. PAD4 regulates gene expression in cancer cells to foster tumorigenesis. For example, PAD4 affects cancer and immune cells [Yuzhalin, A. E., et al. (2018). Nat. Commun., 9(1).].

One of ordinary skill in the art would appreciate that compounds of the invention may exhibit the phenomena of tautomerism, conformational isomerism, geometric isomerism, and/or optical isomerism. For example, the compounds of the invention may include one or more chiral centers and/or double bonds and as a consequence can exist as stereoisomers, such as double-bond isomers (such as, geometric isomers), enantiomers, diastereomers, and mixtures thereof, such as racemic mixtures. As another example, the compounds of the invention may exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the invention encompasses any tautomeric, conformational isomeric, optical isomeric, and/or geometric isomeric forms of the compounds described herein, as well as mixtures of these various different isomeric forms. It is intended that the compounds encompassed herein are, with the exception of forms of isomerism, chemically stable and isolable.

As is understood by one of ordinary skill in the art, certain atoms may occur in more than one isotopic form. For example, hydrogen may occur as protium ($^{1}H$), deuterium ($^{2}H$) and tritium ($^{3}H$), and carbon may occur naturally as three different isotopes, $^{12}C$, $^{13}C$ and $^{14}C$. Examples of isotopes that may be incorporated into the compounds disclosed herein also include, but are not limited to, $^{15}N$, $^{18}O$, $^{17}O$, $^{18}F$, $^{32}F$, $^{33}F$, $^{129}I$, $^{131}I$, $^{123}I$, $^{124}I$, $^{125}I$, or the like. Thus, the disclosed compounds may be enriched in one or more of these isotopes relative to the natural abundance of such isotope. As is known to those of skill in the art, such isotopically enriched compounds may be useful for a variety of purposes. For example, substitution with heavier isotopes such as deuterium ($^2H$) may afford certain therapeutic advantages that result from greater metabolic stability. Substitution with positron emitting isotopes, such as $^{18}F$ may be useful in Positron Emission Tomography (PET) studies. By way of example, deuterium ($^2H$) has a natural abundance of about 0.015%. Accordingly, for approximately every 6,500 hydrogen atoms occurring in nature, there is one deuterium atom. Thus, deuterium containing compounds of the disclosure have deuterium at one or more positions (as the case may be) in an abundance of greater than 0.015%.

Compound of Formula (I)

In one aspect, the present disclosure provides a compound of formula (I):

(I)

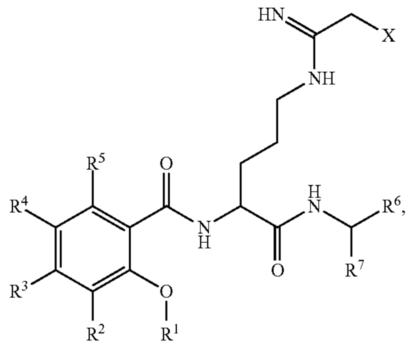

or a pharmaceutically acceptable salt, prodrug, or metabolite thereof, or a solvate or hydrate of any of the foregoing, wherein, X may be halogen; $R^1$ may be selected from the group consisting of optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl; each of $R^2$, $R^3$, $R^4$ and $R^5$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, or $R^2$ and $R^3$ combined with the atoms to which they are attached may form an optionally substituted ring A1, said ring A1 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A1 may be unsubstituted or independently substituted with one or more $R^{9a}$, or $R^3$ and $R^4$ combined with the atoms to which they are attached may form an optionally substituted ring A2, said ring A2 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A2 may be unsubstituted or independently substituted with one or more $R^{9b}$, or $R^4$ and $R^5$ combined with the atoms to which they are attached may form an optionally substituted ring A3, said ring A3 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A3 may be unsubstituted or independently substituted with one or more $R^{9c}$; each of $R^6$ and $R^7$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino; each of $R^{9a}$, $R^{9b}$ and $R^{9c}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, the X may be flouro, chloro, bromo, or iodo. For example, $R^1$ may be optionally substituted ($C_1$-$C_8$) alkyl.

For example, the alkyl may include, but not limited to methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl, 1-hexy, 1-heptyl, 1-octyl or the like.

For example, the carbocycle may include, but not limited to cyclopropyl, cyclobutanyl, cyclopentyl, cyclohexyl, cycloheptyl, cyclooctyl, cyclononyl, cyclodecyl. bicyclo[2.2.1]heptanyl, bicyclo[2.2.2]octanyl, adamantanyl or the like.

For example, the aryl may include, but not limited to phenyl, 2-naphthyl, halogen substituted phenyl, N-linked aliphatic substituted 2-naphthyl and the like; the ($C_6$-$C_{10}$) aryl may include, but not limited to phenyl, halogen substituted phenyl, aliphatic substituted phenyl, aromatic substituted phenyl and the like; the ($C_6$-$C_{10}$) aryl may include, but not limited to 2-naphthyl, substituted 2-naphthyl and the like.

For example, the heteroaryl may include, but not limited to pyridinyl, furanyl halogen substituted pyridinyl and the like.

For example, the pharmaceutically acceptable salt in the disclosure may comprise salts of the compound that modified by non-toxic acids or alkalis and the like.

For example, the pharmaceutical acceptable acid-additive salts of the compound in the disclosure may include, but not limited to inorganic acid salts, such as, hydrochloric acid, hydrobromic acid, nitric acid, carbonic acid, phosphorous acid and the like; organic acid salts, such as, maleic acid, benzenesulfonic acid, p-methyl benzenesulfonic acid, citric acid, tartaric acid, and the like.

For example, the pharmaceutical acceptable alkali-additive salts of the compound in the disclosure may include, but not limited to sodium, potassium, calcium, ammonium or magnesium salts.

For example, the solvate of the compound in the disclosure may comprise the hydrate compound which the compound molecule trap different molar ratio of water molecules, the alcoholate compound which the compound molecule trap different molar ratio of alcohol molecule and the like.

For example, $R^4$ may be selected from the group consisting of hydrogen, halogen, and optionally substituted ($C_6$-$C_{10}$) aryl.

For example, $R^4$ may be selected from the group consisting of F and Cl.

For example, $R^4$ may be optionally substituted phenyl.

For example, $R^4$ may be substituted with one or more $R^8$, each $R^8$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, $R^8$ may be selected from the group consisting of hydrogen, halogen, and optionally substituted ($C_1$-$C_8$) alkyl.

For example, $R^8$ may be selected from the group consisting of F and Cl.

For example, $R^8$ may be optionally substituted methyl.

For example, $R^2$ and $R^3$ combined with the atoms to which they are attached may form an optionally substituted ring A1, said ring A1 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

For example, ring A1 may be optionally substituted ($C_6$-$C_{10}$) aryl.

For example, ring A1 may be optionally substituted phenyl.

For example, ring A1 may be substituted with one or more $R^{9a}$, each $R^{9a}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, $R^{9a}$ may be selected from the group consisting of hydrogen, optionally substituted ($C_1$-$C_8$) alkoxy, and optionally substituted ($C_1$-$C_8$) alkylamino.

For example, $R^{9a}$ may be optionally substituted N,N-dimethylamino.

For example, $R^3$ and $R^4$ combined with the atoms to which they are attached may form an optionally substituted ring A2, said ring A2 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

For example, ring A2 may be optionally substituted ($C_6$-$C_{10}$) aryl.

For example, ring A2 may be optionally substituted phenyl.

For example, ring A2 may be substituted with one or more $R^{9b}$, each $R^{9b}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, $R^{9b}$ may be selected from the group consisting of hydrogen, optionally substituted ($C_1$-$C_8$) alkoxy, and optionally substituted ($C_1$-$C_8$) alkylamino.

For example, $R^{9b}$ may be optionally substituted methoxy.

For example, $R^5$ may be selected from the group consisting of hydrogen, halogen, and optionally substituted ($C_1$-$C_8$) alkoxy.

For example, $R^5$ may be selected from the group consisting of hydrogen, halogen, and optionally substituted methoxy.

For example, $R^5$ may be selected from the group consisting of F and Cl.

For example, $R^5$ may be optionally substituted methoxy.

For example, at least one of $R^6$ and $R^7$ may be not hydrogen.

For example, $R^6$ may be selected from the group consisting of optionally substituted ($C_6$-$C_{10}$) aryl, and optionally substituted ($C_1$-$C_9$) heteroaryl.

For example, $R^6$ may be optionally substituted phenyl.

For example, $R^6$ may be optionally substituted pyridyl.

For example, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy, optionally substituted ($C_1$-$C_8$) alkylamino and optionally substituted group

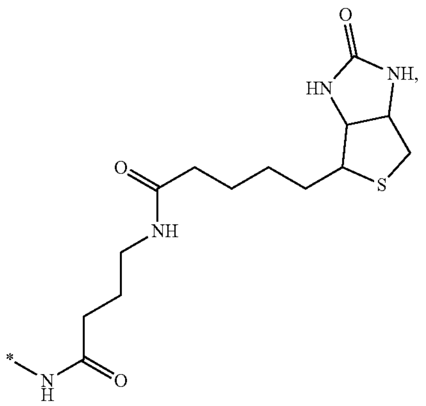 [SMILES: *NC(=O)CCCNC(=O)CCCCC1SCC2NC(=O)NC21]

wherein the asterisk "*" in the structure formulas indicates the available radical ends to be connected.

For example, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

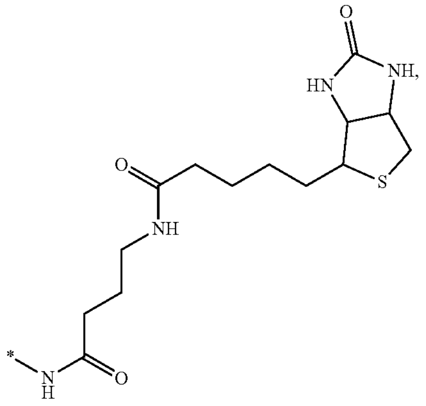 [SMILES: *NC(=O)CCCNC(=O)CCCCC1SCC2NC(=O)NC21]

wherein the asterisk "*" in the structure formulas indicates the available radical ends to be connected.

For example, $R^{10}$ may be selected from the group consisting of F and Cl.

For example, $R^{10}$ may be optionally substituted methyl.

For example, $R^{10}$ may be optionally substituted methoxy.

For example, $R^{10}$ may be optionally substituted group

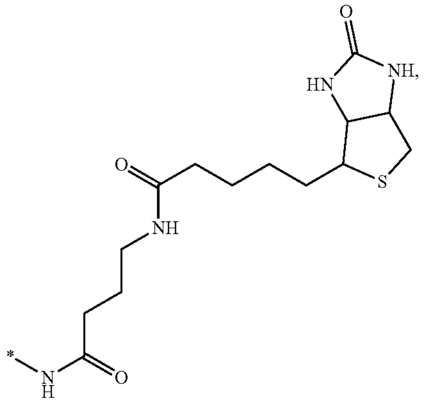 [SMILES: *NC(=O)CCCNC(=O)CCCCC1SCC2NC(=O)NC21]

wherein the asterisk "*" in the structure formulas indicates the available radical ends to be connected.

For example, $R^4$ may be optionally substituted phenyl, $R^4$ may be substituted with one or more $R^8$. For example, $R^4$ may be substituted with 1, 2, 3, 4, or 5 $R^8$.

For example, $R^4$ may be optionally substituted phenyl, $R^4$ may be substituted with one or more $R^8$, $R^8$ may be selected from the group consisting of hydrogen, halogen, and optionally substituted ($C_1$-$C_8$) alkyl.

For example, $R^4$ may be optionally substituted phenyl, $R^4$ may be substituted with one or more $R^8$, $R^8$ may be selected from the group consisting of F and Cl. For example, $R^4$ may be optionally substituted phenyl, $R^4$ may be substituted with one or more $R^8$, $R^8$ may be optionally substituted methyl.

For example, $R^2$ and $R^3$ combined with the atoms to which they are attached may form an optionally substituted ring A1, ring A1 may be optionally substituted ($C_6$-$C_{10}$) aryl.

For example, $R^2$ and $R^3$ combined with the atoms to which they are attached may form an optionally substituted ring A1, ring A1 may be optionally substituted phenyl.

For example, $R^2$ and $R^3$ combined with the atoms to which they are attached may form an optionally substituted ring A1, ring A1 may be substituted with one or more $R^{9a}$. For example, ring A1 may be substituted with 1, 2, 3, 4, 5, 6, 7, or 8 $R^{9a}$.

For example, $R^2$ and $R^3$ combined with the atoms to which they are attached may form an optionally substituted ring A1, ring A1 may be substituted with one or more $R^{9a}$, $R^{9a}$ may be selected from the group consisting of hydrogen, optionally substituted ($C_1$-$C_8$) alkoxy, and optionally substituted ($C_1$-$C_8$) alkylamino.

For example, $R^2$ and $R^3$ combined with the atoms to which they are attached may form an optionally substituted ring A1, ring A1 may be substituted with one or more $R^{9a}$, $R^{9a}$ may be optionally substituted N,N-dimethylamino.

For example, $R^3$ and $R^4$ combined with the atoms to which they are attached may form an optionally substituted ring A2, ring A2 may be optionally substituted ($C_6$-$C_{10}$) aryl.

For example, $R^3$ and $R^4$ combined with the atoms to which they are attached may form an optionally substituted ring A2, ring A2 may be optionally substituted phenyl.

For example, $R^3$ and $R^4$ combined with the atoms to which they are attached may form an optionally substituted ring A2, ring A2 may be substituted with one or more $R^{9b}$. For example, ring A2 may be substituted with 1, 2, 3, 4, 5, 6, 7, or 8 $R^{9b}$.

For example, $R^3$ and $R^4$ combined with the atoms to which they are attached may form an optionally substituted ring A2, ring A2 may be substituted with one or more $R^{9b}$, $R^{9b}$ may be selected from the group consisting of hydrogen, optionally substituted ($C_1$-$C_8$) alkoxy, and optionally substituted ($C_1$-$C_8$) alkylamino.

For example, $R^3$ and $R^4$ combined with the atoms to which they are attached may form an optionally substituted ring A2, ring A2 may be substituted with one or more $R^{9b}$, $R^{9b}$ may be selected from the group consisting of hydrogen, optionally substituted ($C_1$-$C_8$) alkoxy, and optionally substituted methoxy.

For example, $R^6$ may be optionally substituted phenyl, $R^6$ may be substituted with one or more $R^{10}$. For example, $R^6$ may be substituted with 1, 2, 3, 4, or 5 $R^{10}$.

For example, $R^6$ may be optionally substituted pyridyl, $R^6$ may be substituted with one or more $R^{10}$. For example, $R^6$ may be substituted with 1, 2, 3, 4, 5, 6, or 7 $R^{10}$.

For example, $R^6$ may be optionally substituted phenyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

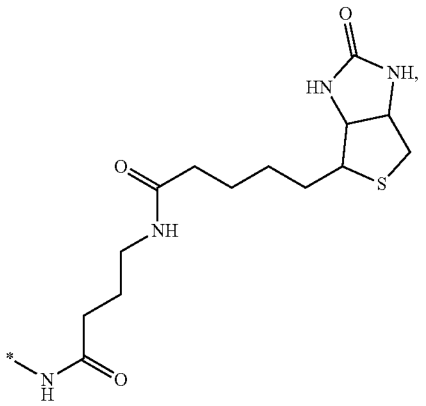 [SMILES: *NC(=O)CCCNC(=O)CCCCC1SCC2NC(=O)NC21]

wherein the asterisk "*" in the structure formulas indicates the available radical ends to be connected.

For example, $R^6$ may be optionally substituted phenyl, $R^6$ may be substituted with one or more $R^{10}$, each $R^{10}$ may be selected from the group consisting of F and Cl.

For example, $R^6$ may be optionally substituted phenyl, $R^6$ may be substituted with one or more $R^{10}$, each $R^{10}$ may be optionally substituted methyl.

For example, $R^6$ may be optionally substituted phenyl, $R^6$ may be substituted with one or more $R^{10}$, each $R^{10}$ may be optionally substituted methoxy.

For example, $R^6$ may be optionally substituted phenyl, $R^6$ may be substituted with one or more $R^{10}$, each $R^{10}$ may be optionally substituted group

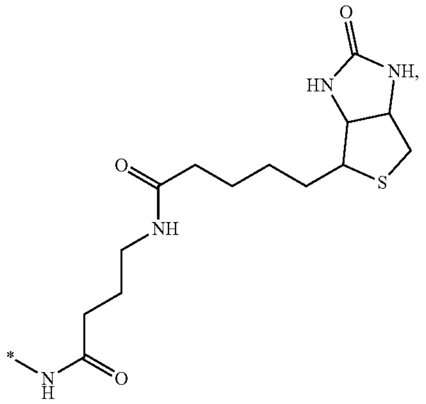 [SMILES: *NC(=O)CCCNC(=O)CCCCC1SCC2NC(=O)NC21]

wherein the asterisk "*" in the structure formulas indicates the available radical ends to be connected.

For example, $R^6$ may be optionally substituted pyridyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

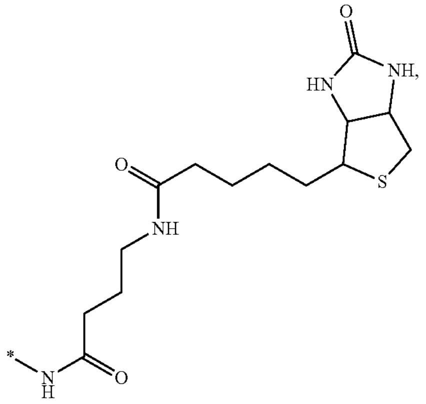 [SMILES: *NC(=O)CCCNC(=O)CCCCC1SCC2NC(=O)NC21]

wherein the asterisk "*" in the structure formulas indicates the available radical ends to be connected.

For example, $R^6$ may be optionally substituted pyridyl, $R^6$ may be substituted with one or more $R^{10}$, each $R^{10}$ may be selected from the group consisting of F and Cl.

For example, $R^6$ may be optionally substituted pyridyl, $R^6$ may be substituted with one or more $R^{10}$, each $R^{10}$ may be optionally substituted methyl.

For example, $R^6$ may be optionally substituted pyridyl, $R^6$ may be substituted with one or more $R^{10}$, each $R^{10}$ may be optionally substituted methoxy.

For example, $R^6$ may be optionally substituted pyridyl, $R^6$ may be substituted with one or more $R^{10}$, each $R^{10}$ may be optionally substituted group

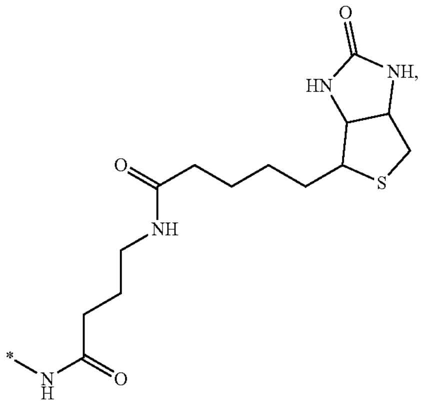 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^2$ and $R^3$ combined with the atoms to which they are attached may form an optionally substituted ring A1, ring A1 may be optionally substituted ($C_6$-$C_{10}$) aryl, ring A1 may be substituted with one or more $R^{9a}$, $R^{9a}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted ($C_6$-$C_{10}$) aryl, and optionally substituted ($C_1$-$C_9$) heteroaryl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

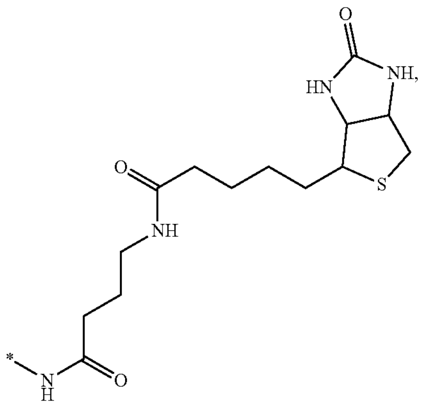 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^3$ and $R^4$ combined with the atoms to which they are attached may form an optionally substituted ring A2, ring A2 may be optionally substituted ($C_6$-$C_{10}$) aryl, ring A2 may be substituted with one or more $R^{9b}$, each $R^{9b}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted ($C_6$-$C_{10}$) aryl, and optionally substituted ($C_1$-$C_9$) heteroaryl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

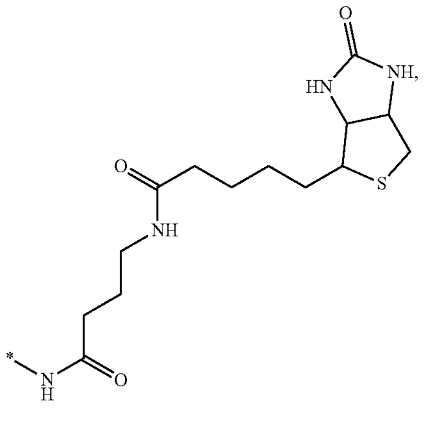 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^2$ and $R^3$ combined with the atoms to which they are attached may form an optionally substituted ring A1, ring A1 may be optionally substituted phenyl, ring A1 may be substituted with one or more $R^{9a}$, $R^{9a}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted phenyl, and optionally substituted pyridyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

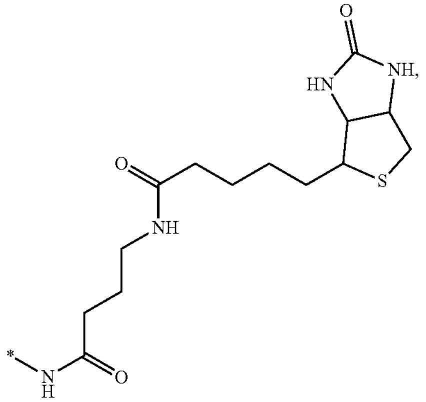 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^3$ and $R^4$ combined with the atoms to which they are attached may form an optionally substituted ring A2, ring A2 may be optionally substituted phenyl, ring A2 may be substituted with one or more $R^{9b}$, each $R^{9b}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted phenyl, and optionally substituted pyridyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

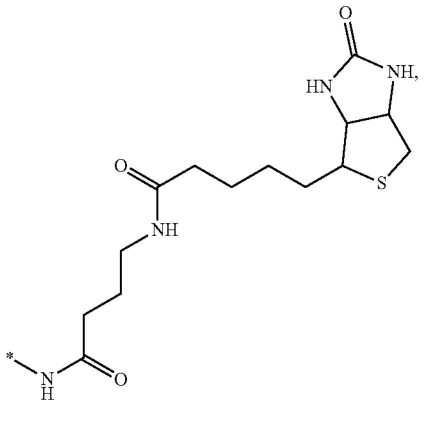 [SMILES: *NC(=O)CCCNC(=O)CCCCC1SCC2NC(=O)NC21]

wherein the asterisk "*" in the structure formulas indicates the available radical ends to be connected.

In one aspect, the present disclosure provides a compound of formula (II):

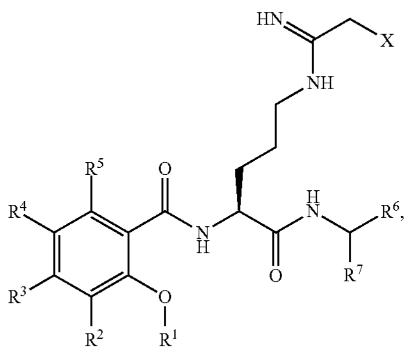

(II)

or a pharmaceutically acceptable salt, prodrug, or metabolite thereof, or a solvate or hydrate of any of the foregoing, wherein, X may be halogen; $R^1$ may be selected from the group consisting of optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl; each of $R^2$, $R^3$, $R^4$ and $R^5$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, or $R^2$ and $R^3$ combined with the atoms to which they are attached may form an optionally substituted ring A1, said ring A1 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A1 may be unsubstituted or independently substituted with one or more $R^{9a}$, or $R^3$ and $R^4$ combined with the atoms to which they are attached may form an optionally substituted ring A2, said ring A2 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A2 may be unsubstituted or independently substituted with one or more $R^{9b}$, or $R^4$ and $R^5$ combined with the atoms to which they are attached may form an optionally substituted ring A3, said ring A3 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A3 may be unsubstituted or independently substituted with one or more $R^{9c}$; each of $R^6$ and $R^7$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino; each of $R^{9a}$, $R^{9b}$ and $R^{9c}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, the X may be flouro, chloro, bromo, or iodo.

For example, $R^1$ may be optionally substituted ($C_1$-$C_8$) alkyl.

For example, the alkyl may include, but not limited to methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl, 1-hexy, 1-heptyl, 1-octyl or the like.

For example, the carbocycle may include, but not limited to cyclopropyl, cyclobutanyl, cyclopentyl, cyclohexyl, cycloheptyl, cyclooctyl, cyclononyl, cyclodecyl. bicyclo [2.2.1]heptanyl, bicyclo[2.2.2]octanyl, adamantanyl or the like.

For example, the aryl may include, but not limited to phenyl, 2-naphthyl, halogen substituted phenyl, N-linked aliphatic substituted 2-naphthyl and the like; the ($C_6$-$C_{10}$) aryl may include, but not limited to phenyl, halogen substituted phenyl, aliphatic substituted phenyl, aromatic substituted phenyl and the like; the ($C_6$-$C_{10}$) aryl may include, but not limited to 2-naphthyl, substituted 2-naphthyl and the like.

For example, the heteroaryl may include, but not limited to pyridinyl, furanyl halogen substituted pyridinyl and the like.

For example, the pharmaceutically acceptable salt in the disclosure may comprise salts of the compound that modified by non-toxic acids or alkalis and the like.

For example, the pharmaceutical acceptable acid-additive salts of the compound in the disclosure may include, but not limited to inorganic acid salts, such as, hydrochloric acid, hydrobromic acid, nitric acid, carbonic acid, phosphorous acid and the like; organic acid salts, such as, maleic acid, benzenesulfonic acid, p-methyl benzenesulfonic acid, citric acid, tartaric acid, and the like.

For example, the pharmaceutical acceptable alkali-additive salts of the compound in the disclosure may include, but not limited to sodium, potassium, calcium, ammonium or magnesium salts.

For example, the solvate of the compound in the disclosure may comprise the hydrate compound which the compound molecule trap different molar ratio of water molecules, the alcoholate compound which the compound molecule trap different molar ratio of alcohol molecule and the like.

For example, $R^4$ may be selected from the group consisting of hydrogen, halogen, and optionally substituted ($C_6$-$C_{10}$) aryl.

For example, $R^4$ may be selected from the group consisting of F and Cl.

For example, $R^4$ may be optionally substituted phenyl.

For example, $R^4$ may be substituted with one or more $R^8$, each $R^8$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, $R^8$ may be selected from the group consisting of hydrogen, halogen, and optionally substituted ($C_1$-$C_8$) alkyl.

For example, $R^8$ may be selected from the group consisting of F and Cl.

For example, $R^8$ may be optionally substituted methyl.

For example, $R^2$ and $R^3$ combined with the atoms to which they are attached may form an optionally substituted ring A1, said ring A1 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

For example, ring A1 may be optionally substituted ($C_6$-$C_{10}$) aryl.

For example, ring A1 may be optionally substituted phenyl.

For example, ring A1 may be substituted with one or more $R^{9a}$, each $R^{9a}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, $R^{9a}$ may be selected from the group consisting of hydrogen, optionally substituted ($C_1$-$C_8$) alkoxy, and optionally substituted ($C_1$-$C_8$) alkylamino.

For example, $R^{9a}$ may be optionally substituted N,N-dimethylamino.

For example, $R^3$ and $R^4$ combined with the atoms to which they are attached may form an optionally substituted ring A2, said ring A2 may be selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

For example, ring A2 may be optionally substituted ($C_6$-$C_{10}$) aryl.

For example, ring A2 may be optionally substituted phenyl.

For example, ring A2 may be substituted with one or more $R^{9b}$, each $R^{9b}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

For example, $R^{9b}$ may be selected from the group consisting of hydrogen, optionally substituted ($C_1$-$C_8$) alkoxy, and optionally substituted ($C_1$-$C_8$) alkylamino.

For example, $R^{9b}$ may be optionally substituted methoxy.

For example, $R^5$ may be selected from the group consisting of hydrogen, halogen, and optionally substituted ($C_1$-$C_8$) alkoxy.

For example, $R^5$ may be selected from the group consisting of hydrogen, halogen, and optionally substituted methoxy.

For example, $R^5$ may be selected from the group consisting of F and Cl.

For example, $R^5$ may be optionally substituted methoxy.

For example, at least one of $R^6$ and $R^7$ may be not hydrogen.

For example, $R^6$ may be selected from the group consisting of optionally substituted ($C_6$-$C_{10}$) aryl, and optionally substituted ($C_1$-$C_9$) heteroaryl.

For example, $R^6$ may be optionally substituted phenyl.

For example, $R^6$ may be optionally substituted pyridyl.

For example, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy, optionally substituted ($C_1$-$C_8$) alkylamino and optionally substituted group

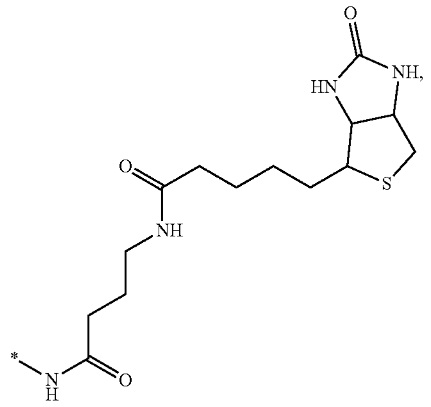 [SMILES: *NC(=O)CCCNC(=O)CCCCC1SCC2NC(=O)NC21]

wherein the asterisk "*" in the structure formulas indicates the available radical ends to be connected.

For example, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

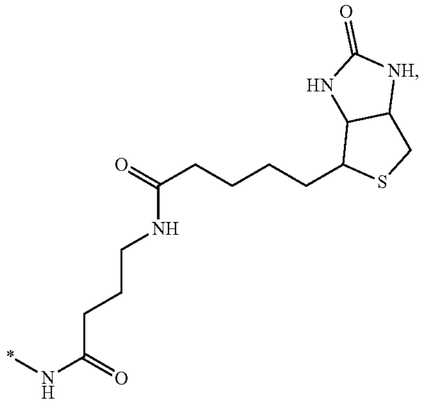 [SMILES: *NC(=O)CCCNC(=O)CCCCC1SCC2NC(=O)NC21]

wherein the asterisk "*" in the structure formulas indicates the available radical ends to be connected.

For example, $R^{10}$ may be selected from the group consisting of F and Cl.

For example, $R^{10}$ may be optionally substituted methyl.

For example, $R^{10}$ may be optionally substituted methoxy.

For example, $R^{10}$ may be optionally substituted group

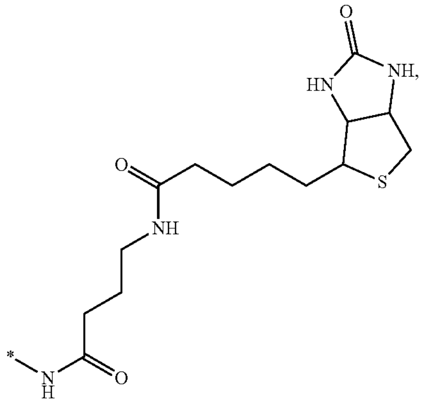 [SMILES: *NC(=O)CCCNC(=O)CCCCC1SCC2NC(=O)NC21]

wherein the asterisk "*" in the structure formulas indicates the available radical ends to be connected.

For example, $R^4$ may be optionally substituted phenyl, $R^4$ may be substituted with one or more $R^8$. For example, $R^4$ may be substituted with 1, 2, 3, 4, or 5 $R^8$.

For example, $R^4$ may be optionally substituted phenyl, $R^4$ may be substituted with one or more $R^8$, $R^8$ may be selected from the group consisting of hydrogen, halogen, and optionally substituted ($C_1$-$C_8$) alkyl.

For example, $R^4$ may be optionally substituted phenyl, $R^4$ may be substituted with one or more $R^8$, $R^8$ may be selected from the group consisting of F and Cl. For example, $R^4$ may be optionally substituted phenyl, $R^4$ may be substituted with one or more $R^8$, $R^8$ may be optionally substituted methyl.

For example, $R^2$ and $R^3$ combined with the atoms to which they are attached may form an optionally substituted ring A1, ring A1 may be optionally substituted ($C_6$-$C_{10}$) aryl.

For example, $R^2$ and $R^3$ combined with the atoms to which they are attached may form an optionally substituted ring A1, ring A1 may be optionally substituted phenyl.

For example, $R^2$ and $R^3$ combined with the atoms to which they are attached may form an optionally substituted ring A1, ring A1 may be substituted with one or more $R^{9a}$. For example, ring A1 may be substituted with 1, 2, 3, 4, 5, 6, 7, or 8 $R^{9a}$.

For example, $R^2$ and $R^3$ combined with the atoms to which they are attached may form an optionally substituted ring A1, ring A1 may be substituted with one or more $R^{9a}$, $R^{9a}$ may be selected from the group consisting of hydrogen, optionally substituted ($C_1$-$C_8$) alkoxy, and optionally substituted ($C_1$-$C_8$) alkylamino.

For example, $R^2$ and $R^3$ combined with the atoms to which they are attached may form an optionally substituted ring A1, ring A1 may be substituted with one or more $R^{9a}$, $R^{9a}$ may be optionally substituted N,N-dimethylamino.

For example, $R^3$ and $R^4$ combined with the atoms to which they are attached may form an optionally substituted ring A2, ring A2 may be optionally substituted ($C_6$-$C_{10}$) aryl.

For example, $R^3$ and $R^4$ combined with the atoms to which they are attached may form an optionally substituted ring A2, ring A2 may be optionally substituted phenyl.

For example, $R^3$ and $R^4$ combined with the atoms to which they are attached may form an optionally substituted ring A2, ring A2 may be substituted with one or more $R^{9b}$. For example, ring A2 may be substituted with 1, 2, 3, 4, 5, 6, 7, or 8 $R^{9b}$.

For example, $R^3$ and $R^4$ combined with the atoms to which they are attached may form an optionally substituted ring A2, ring A2 may be substituted with one or more $R^{9b}$, $R^{9b}$ may be selected from the group consisting of hydrogen, optionally substituted ($C_1$-$C_8$) alkoxy, and optionally substituted ($C_1$-$C_8$) alkylamino.

For example, $R^3$ and $R^4$ combined with the atoms to which they are attached may form an optionally substituted ring A2, ring A2 may be substituted with one or more $R^{9b}$, $R^{9b}$ may be selected from the group consisting of hydrogen, optionally substituted ($C_1$-$C_8$) alkoxy, and optionally substituted methoxy.

For example, $R^6$ may be optionally substituted phenyl, $R^6$ may be substituted with one or more $R^{10}$. For example, $R^6$ may be substituted with 1, 2, 3, 4, or 5 $R^{10}$.

For example, $R^6$ may be optionally substituted pyridyl, $R^6$ may be substituted with one or more $R^{10}$. For example, $R^6$ may be substituted with 1, 2, 3, 4, 5, 6, or 7 $R^{10}$.

For example, $R^6$ may be optionally substituted phenyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

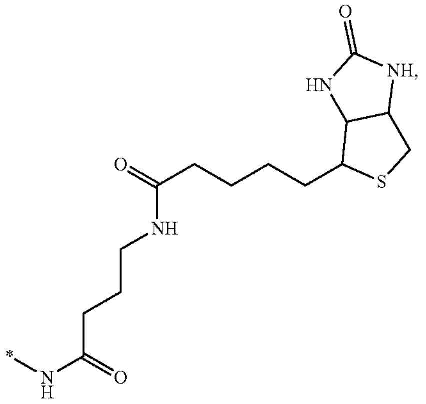 [SMILES: *NC(=O)CCCNC(=O)CCCCC1SCC2NC(=O)NC21]

wherein the asterisk "*" in the structure formulas indicates the available radical ends to be connected.

For example, $R^6$ may be optionally substituted phenyl, $R^6$ may be substituted with one or more $R^{10}$, each $R^{10}$ may be selected from the group consisting of F and Cl.

For example, $R^6$ may be optionally substituted phenyl, $R^6$ may be substituted with one or more $R^{10}$, each $R^{10}$ may be optionally substituted methyl.

For example, $R^6$ may be optionally substituted phenyl, $R^6$ may be substituted with one or more $R^{10}$, each $R^{10}$ may be optionally substituted methoxy.

For example, $R^6$ may be optionally substituted phenyl, $R^6$ may be substituted with one or more $R^{10}$, each $R^{10}$ may be optionally substituted group

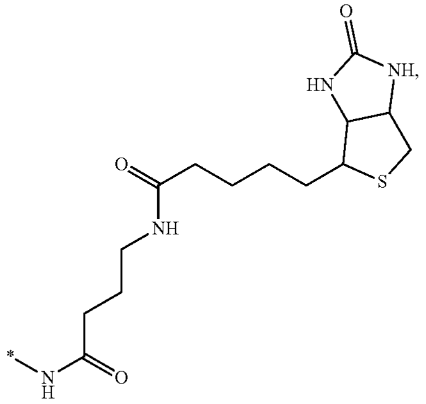 [SMILES: *NC(=O)CCCNC(=O)CCCCC1SCC2NC(=O)NC21]

wherein the asterisk "*" in the structure formulas indicates the available radical ends to be connected.

For example, $R^6$ may be optionally substituted pyridyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

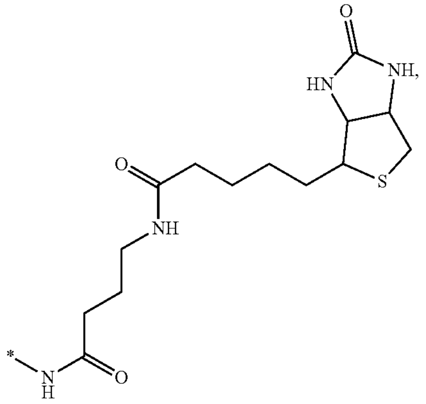 [SMILES: *NC(=O)CCCNC(=O)CCCCC1SCC2NC(=O)NC21]

wherein the asterisk "*" in the structure formulas indicates the available radical ends to be connected.

For example, $R^6$ may be optionally substituted pyridyl, $R^6$ may be substituted with one or more $R^{10}$, each $R^{10}$ may be selected from the group consisting of F and Cl.

For example, $R^6$ may be optionally substituted pyridyl, $R^6$ may be substituted with one or more $R^{10}$, each $R^{10}$ may be optionally substituted methyl.

For example, $R^6$ may be optionally substituted pyridyl, $R^6$ may be substituted with one or more $R^{10}$, each $R^{10}$ may be optionally substituted methoxy.

For example, $R^6$ may be optionally substituted pyridyl, $R^6$ may be substituted with one or more $R^{10}$, each $R^{10}$ may be optionally substituted group

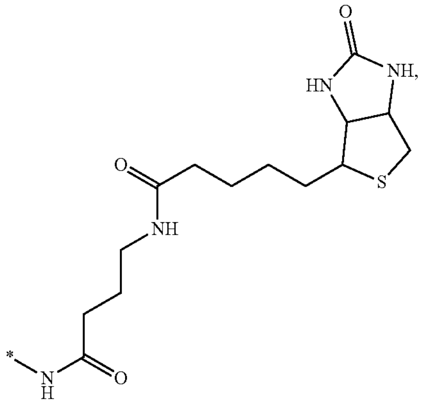 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^2$ and $R^3$ combined with the atoms to which they are attached may form an optionally substituted ring A1, ring A1 may be optionally substituted ($C_6$-$C_{10}$) aryl, ring A1 may be substituted with one or more $R^{9a}$, $R^{9a}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted ($C_6$-$C_{10}$) aryl, and optionally substituted ($C_1$-$C_9$) heteroaryl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

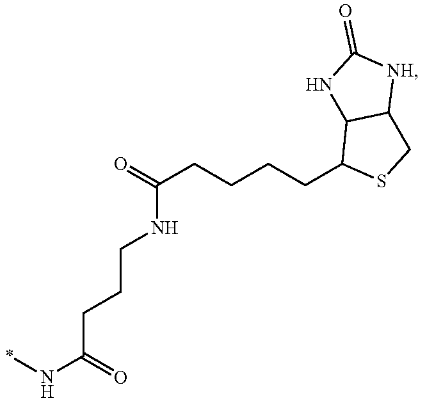 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^3$ and $R^4$ combined with the atoms to which they are attached may form an optionally substituted ring A2, ring A2 may be optionally substituted ($C_6$-$C_{10}$) aryl, ring A2 may be substituted with one or more $R^{9b}$, each $R^{9b}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted ($C_6$-$C_{10}$) aryl, and optionally substituted ($C_1$-$C_9$) heteroaryl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

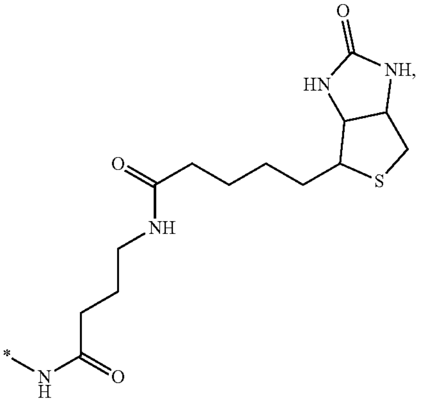 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^2$ and $R^3$ combined with the atoms to which they are attached may form an optionally substituted ring A1, ring A1 may be optionally substituted phenyl, ring A1 may be substituted with one or more $R^{9a}$, $R^{9a}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted phenyl, and optionally substituted pyridyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

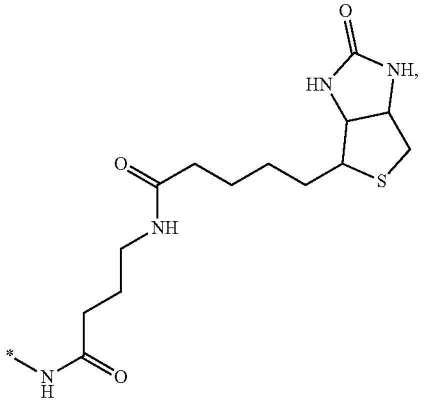 [SMILES: *NC(=O)CCCNC(=O)CCCCC1SCC2NC(=O)NC21]

wherein the asterisk "*" in the structure formulas indicates the available radical ends to be connected.

For example, the X may be flouro, chloro, bromo, or iodo, $R^1$ may be optionally substituted ($C_1$-$C_8$) alkyl, $R^4$ may be substituted with one or more $R^8$, $R^8$ may be selected from the group consisting of hydrogen, halogen, and optionally substituted ($C_1$-$C_8$) alkyl, $R^3$ and $R^4$ combined with the atoms to which they are attached may form an optionally substituted ring A2, ring A2 may be optionally substituted phenyl, ring A2 may be substituted with one or more $R^{9b}$, each $R^{9b}$ may be selected from the group consisting of hydrogen, optionally substituted ($C_1$-$C_8$) alkoxy, and optionally substituted ($C_1$-$C_8$) alkylamino, $R^5$ may be selected from the group consisting of hydrogen, halogen, and optionally substituted ($C_1$-$C_8$) alkoxy, $R^6$ may be selected from the group consisting of optionally substituted phenyl, and optionally substituted pyridyl, $R^6$ may be substituted with one or more $R^{10}$, each $R^{10}$ may be independently selected from the group consisting of hydrogen, halogen, optionally substituted ($C_1$-$C_8$) alkyl, optionally substituted ($C_1$-$C_8$) alkoxy and optionally substituted group

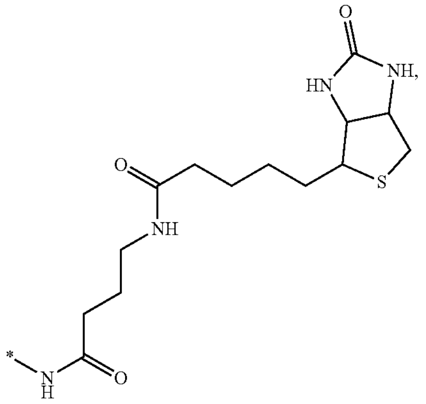 [SMILES: *NC(=O)CCCNC(=O)CCCCC1SCC2NC(=O)NC21]

wherein the asterisk "*" in the structure formulas indicates the available radical ends to be connected.

For example, the compound of the disclosure may be selected from the group consisting of:
EX-1
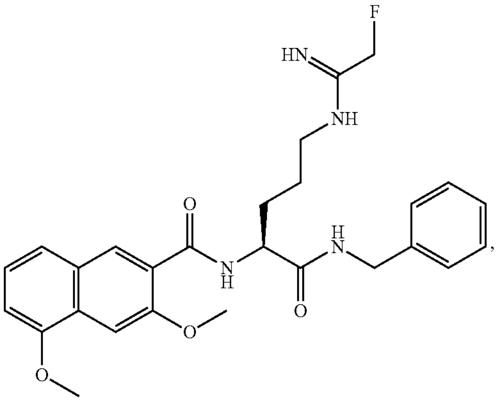
EX-2
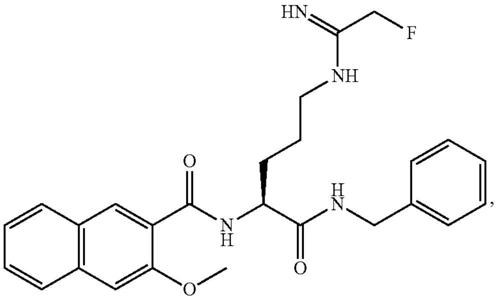
EX-3
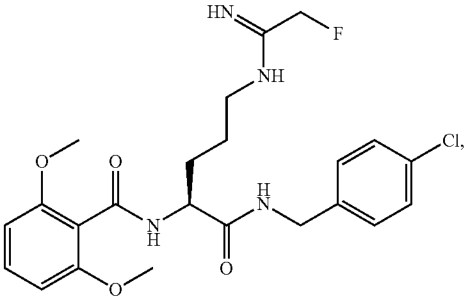
EX-4
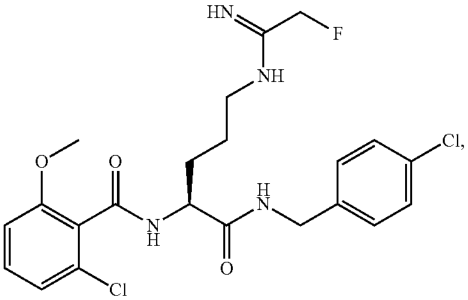
EX-5
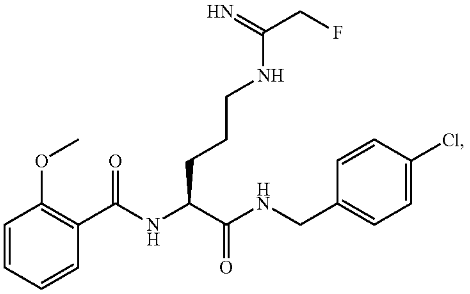
EX-6
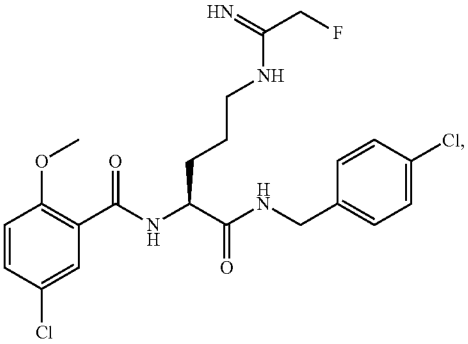
EX-7
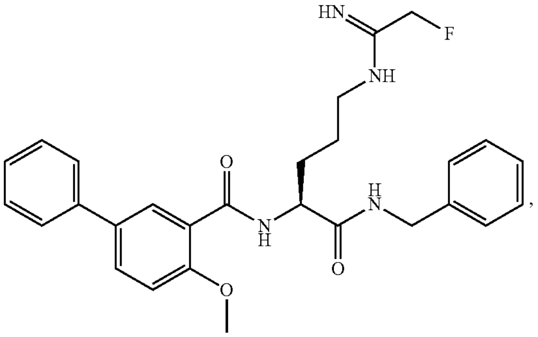
EX-8
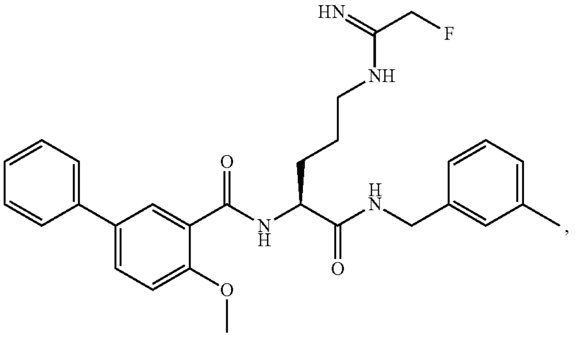

-continued
EX-9
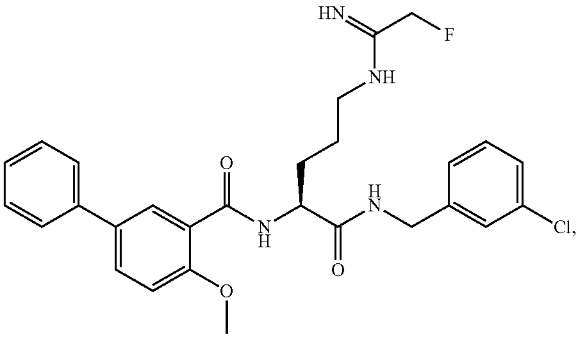
,
EX-10
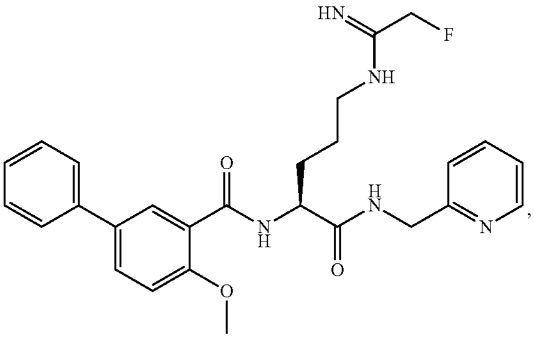
,
EX-11
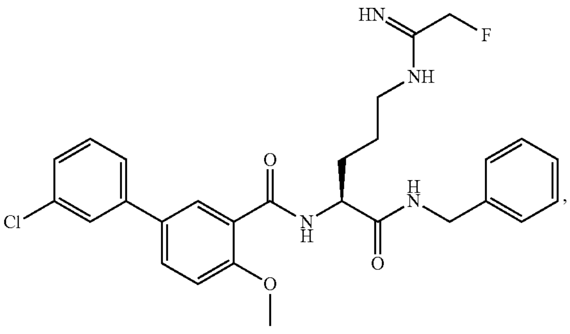
,
EX-12
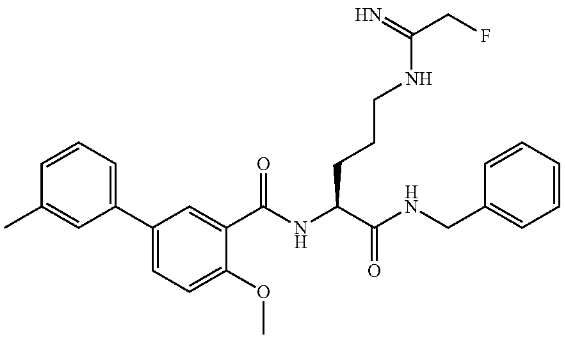
,
EX-13
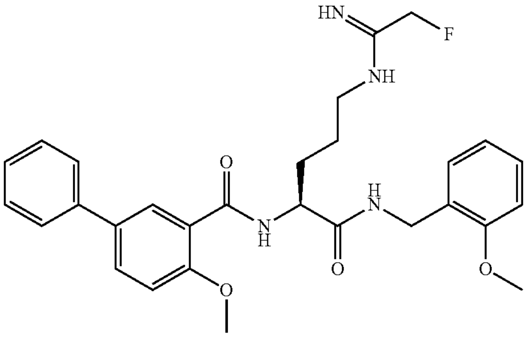
,
EX-14
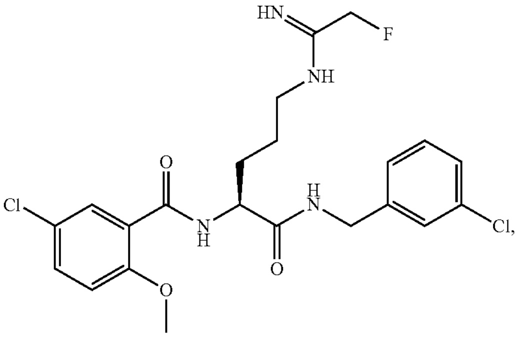
,
EX-15
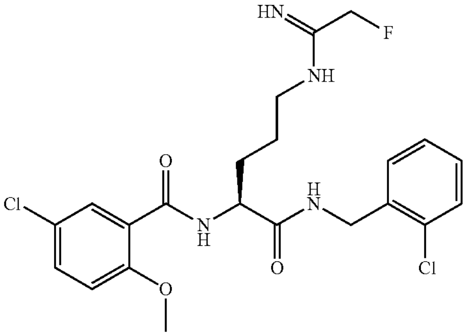
,
EX-16
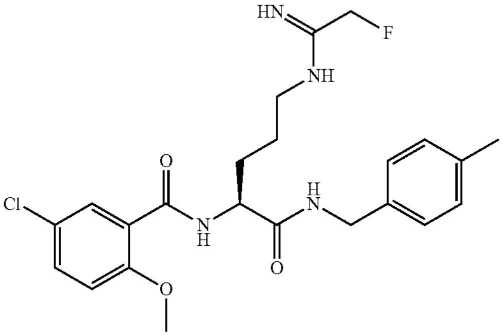
, -continued
EX-17
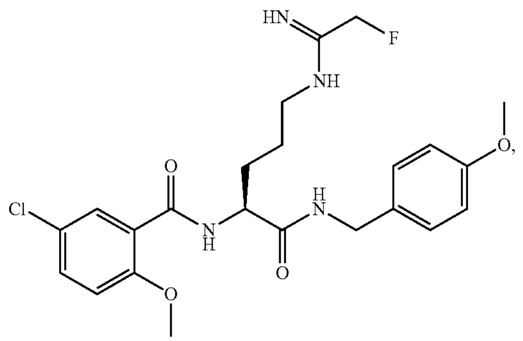
EX-18
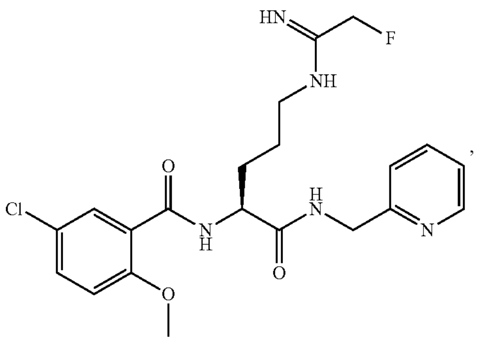
EX-19
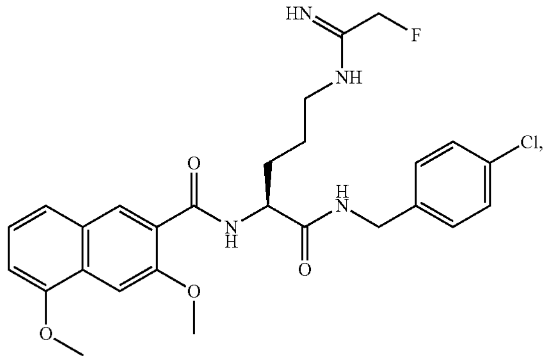
EX-20
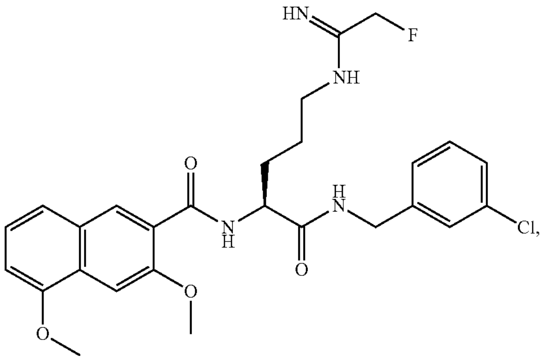
EX-21
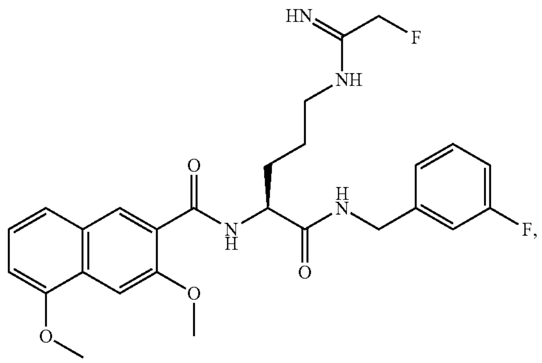
EX-22
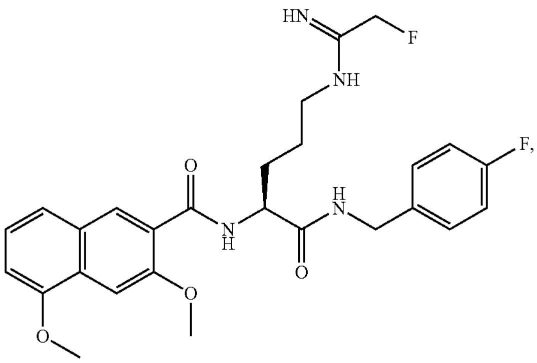
EX-23
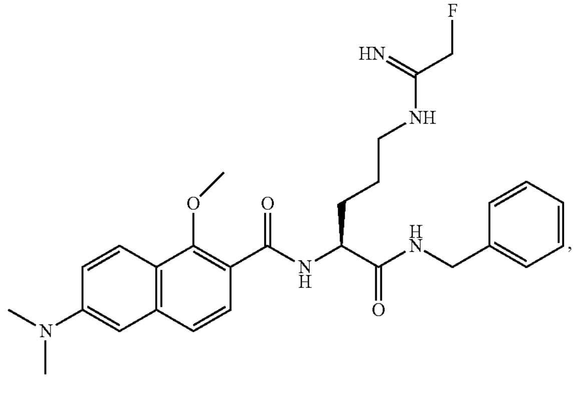
and -continued

EX-24

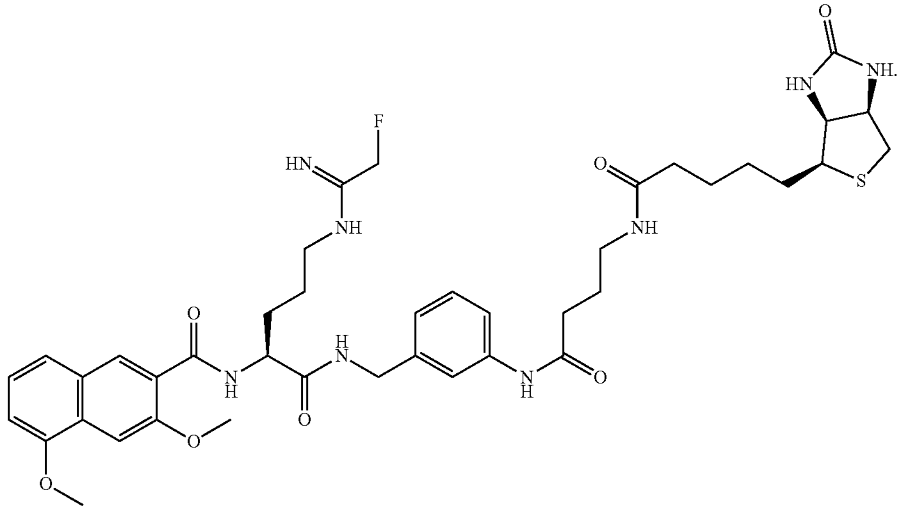

In one aspect, the present disclosure provides a composition comprising the compound of the disclosure, or a pharmaceutically acceptable salt or solvate thereof.

For example, the composition may include compound of formula (I), compound of formula (II), compound selected from EX-1 to EX-24.

For example, the composition may include the pharmaceutically acceptable salt of compound (I), the pharmaceutically acceptable salt of compound (II), the pharmaceutically acceptable salt of compound selected from EX-1 to EX-24.

For example, the composition may include the solvate compound of formula (I), the solvate compound of formula (II), the solvate compound selected from EX-1 to EX-24.

For example, the composition further comprising a pharmaceutically acceptable carrier. For example, the carrier may include, but not limited to sugars, such as lactose, glucose and sucrose; starches, such as corn starch and potato starch; cellulose, and its derivatives, such as sodium carboxymethyl cellulose, ethyl cellulose and cellulose acetate; powdered tragacanthin; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

For example, the composition comprises an effective amount of the compound of the disclosure, or a pharmaceutically acceptable salt of the compound of the disclosure or solvate compound of the disclosure.

For example, the therapeutically effective amount may mean an amount of the subject composition that is enough to treat, ameliorate, or prevent an identified disease or condition, or to exhibit a detectable therapeutic or inhibitory effect. The specific amount/concentration of the active agent comprised may vary according to the method of administration and the need of a patient, and can be determined based on e.g., volume, viscosity, and/or body weight of a patient etc. It shall be understood that the specific doses may be conveniently adjusted by a skilled person in the art (e.g., a doctor or a pharmacist) based on conditions of a specific patient, formulation, and/or disease.

In one aspect, the present disclosure provides a method for preparing a PAD inhibitor, comprising providing a compound of formula (I), compound of formula (II), compound selected from EX-1 to EX-24, the pharmaceutically acceptable salt of compound (I), the pharmaceutically acceptable salt of compound (II), the pharmaceutically acceptable salt of compound selected from EX-1 to EX-24 or the solvate compound of formula (I), the solvate compound of formula (II), the solvate compound selected from EX-1 to EX-24.

For example, the PAD inhibitor may be an inhibitor which could inhibit the function of PAD, such as PAD1, PAD2, PADS, PAD4, PAD6 and the like. The function of PAD may be catalyzing the conversion of arginine residues to citrulline residues.

For example, the PAD inhibitor may be a PAD2 or PAD4 inhibitor.

In one aspect, the present disclosure provides the compound, or a pharmaceutically acceptable salt of solvate thereof, for use in treating a disease or disorder. In one aspect, the present disclosure a method of treating a disease or disorder comprising administering to a subject in need thereof the compound, or a pharmaceutically acceptable salt of solvate thereof. In some embodiments, wherein said disease or disorder may be neoplastic disease or autoimmune disease.

In one aspect, the present disclosure provides a use of the compound of the disclosure, or a pharmaceutically acceptable salt or solvate thereof, in the preparation of a medicament for preventing and/or treating a disease or disorder. In some embodiments, wherein said disease or disorder may be neoplastic disease or autoimmune disease. In some embodiments, said disease or disorder may be selected from the group consisting of solid tumor and blood tumor. In some embodiments, said disease or disorder may be selected from the group consisting of lung cancer, blood cancer, breast cancer with or without lung metastasis, colon cancer with or without liver metastasis, rheumatoid arthritis, ischemia-reperfusion injury, and immune response induced during transplant rejection. In some embodiments, the medicament may further comprise one or more additional pharmaceutically active agents. In some embodiments, said agent may be a checkpoint inhibitor.

In one aspect, the present disclosure provides the compound of the disclosure, or a pharmaceutically acceptable salt or solvate thereof, for use in preventing and/or treating a disease or disorder. In some embodiments, wherein said disease or disorder may be neoplastic disease or autoimmune disease. In some embodiments, said disease or disorder may be selected from the group consisting of solid tumor and blood tumor. In some embodiments, said disease or disorder may be selected from the group consisting of lung cancer, blood cancer, breast cancer with or without lung metastasis, colon cancer with or without liver metastasis, rheumatoid arthritis, ischemia-reperfusion injury, and immune response induced during transplant rejection. In some embodiments, the present disclosure provides the compound of the disclosure, or a pharmaceutically acceptable salt or solvate thereof and one or more additional therapeutics including radiotherapy, chemotherapy, cell therapy and pharmaceutically active agents, for use in preventing and/or treating a disease or disorder. In some embodiments, said agent may be a checkpoint inhibitor.

In one aspect, the present disclosure provides a method for preventing and/or treating a disease or disorder, comprising administering to a subject in need thereof a compound of the disclosure, or a pharmaceutically acceptable salt or solvate thereof. In some embodiments, wherein said disease or disorder may be neoplastic disease or autoimmune disease. In some embodiments, said disease or disorder may be selected from the group consisting of solid tumor and blood tumor. In some embodiments, said disease or disorder may be selected from the group consisting of lung cancer, blood cancer, breast cancer with or without lung metastasis, colon cancer with or without liver metastasis, rheumatoid arthritis, ischemia-reperfusion injury, and immune response induced during transplant rejection. In some embodiments, the method may further comprise administering to a subject in need thereof one or more additional therapeutics including radiotherapy, chemotherapy, cell therapy and pharmaceutically active agents.

For example, the administration form may comprise oral administration as a tablet, capsule, pill, powder, sustained release formulations, solution, suspension and the like; parenteral injection as a sterile solution, suspension or emulsion and the like; topical administration as an ointment or cream and like; or rectal administration as a suppository and the like.

Abbreviations:

AcOH Acetic acid
aq. Aqueous
br broad
Bn Benzyl
d doublet
CDI Carbonyldiimidazole
DBU 1,8-Diazabicyclo[5.4.0]undec-7-ene
DCC N,N'-Dicyclohexylcarbodiimide
DCE 1,2-Dichloroethane
DCM Dichloromethane
DIEA, DIPEA N,N-diisopropylethylamine
DME Dimethoxyethane
DMF N,N-Dimethylformamide
DMSO Dimethyl sulphoxide
EA, EtOAc Ethyl Acetate
EDCI 1,3-Propanediamine, N3 -(ethylcarbonimidoyl)-N1,N1-dimethyl-, hydrochloride
eq., equiv. Equivalent
HATU N,N,N',N'-Tetramethyl-O-(7-azabenzotriazol-1-yl)uronium-hexafluorophospate
HOBT Hydroxybenzotriazole
IPA Isopropanol
NBS N-Bromosuccinimide
NMR Nuclear magnetic resonance
PE Petroleum ether
prep-HPLC Preparative High Pressure Liquid Chromatography
prep-TLC Preparation Thin-layer chromatography
RT, rt Room temperature
s singlet
t triplet
TEA Triethylamine
TLC Thin-layer chromatography
THF Tetrahydrofuran
TFA Trifluoroacetic acid
V, v Volume

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Synthesis of (S)-N-(1-(benzylamino)-5-(2-fluoroacetimidamido)-1-oxopentan-2-yl)-3,5-dimethoxy-2-naphthamide (EX-1)

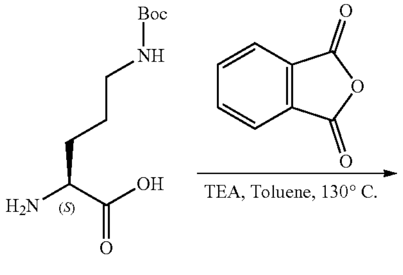

-continued

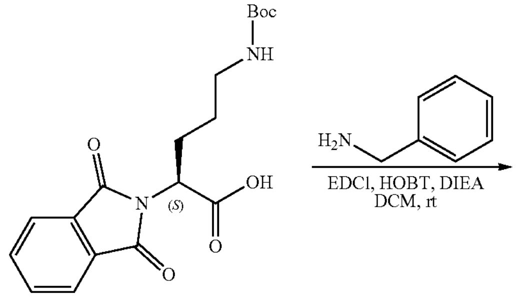

1-1

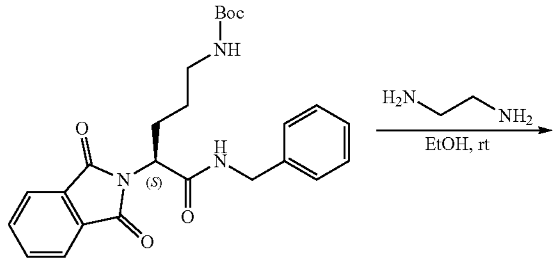

1-2

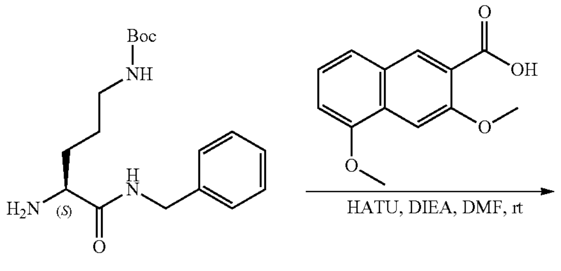

1-3

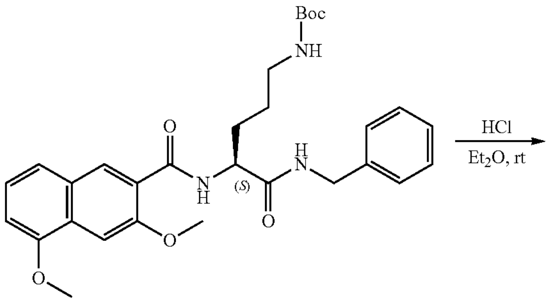

1-4

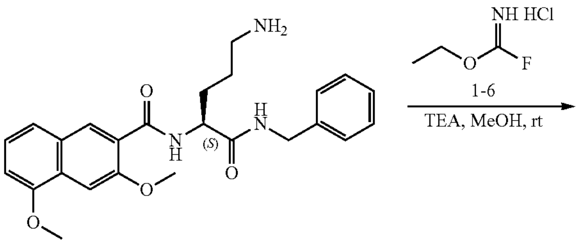

1-5

-continued

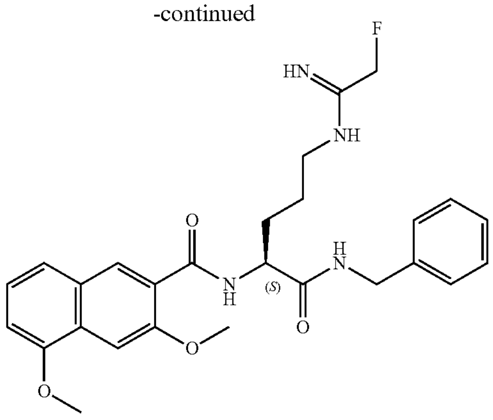

EX-1

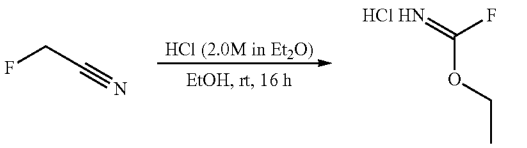

1-6

Step 1:

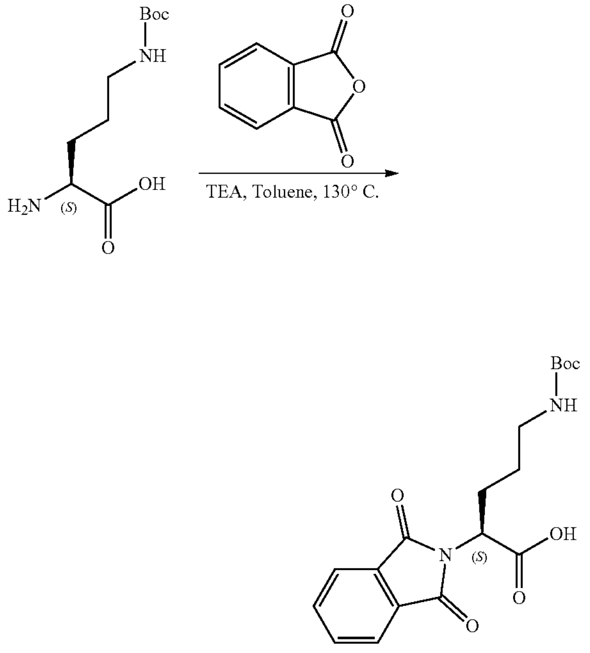

1-1

To a suspension of (5)-2-amino-5-((tert-butoxycarbonyl) amino)pentanoic acid (5.00 g, 21.5 mmol) and phthalic anhydride (3.50 g, 23.7 mmol) in toluene (60 mL) at 0° C. was added TEA (2.4 g, 23.7 mmol). The mixture was stirred at 130° C. under $N_2$ for 16 hours. The reaction mixture was concentrated and diluted with ethyl acetate (150 mL), washed with water (50 mL×2), brine (50 mL) and concentrated to afford crude compound 1-1 (6.5 g) as a white solid, yield: 83%. The crude product was used directly without further purification. MS (ESI) m/z=385.1 $[M+Na]^+$.

Step 2:

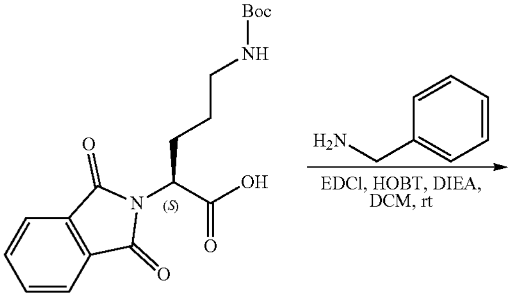

1-1

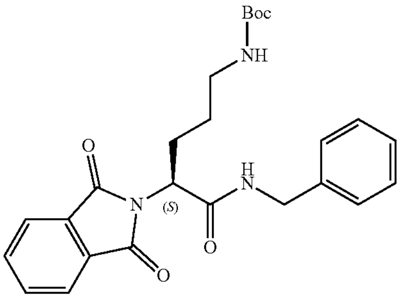

1-2

To a solution of compound 1-1 (6.00 g, 16.5 mmol), DIEA (4.26 g, 33.1 mmol), EDCI (4.76 g, 24.8 mmol) and HOBT (3.36 g, 24.8 mmol) in dichloromethane (100 mL) was added benzylamine (2.13 g, 19.8 mmol). The mixture was stirred at room temperature for 14 hours. The mixture was quenched with water (100 mL) and extracted with dichloromethane (100 mL×2). The organic layers were washed with brine (100 mL), dried over anhydrous $Na_2SO_4$ and concentrated under vacuum to afford crude product, which was purified by silica gel chromatography (elution gradient: petroleum ether/EA, 3/1, v/v) to afford compound 1-2 (4.5 g) as a yellow solid, yield: 60%. MS (ESI) m/z=452.1 $[M+H]^+$.

Step 3:

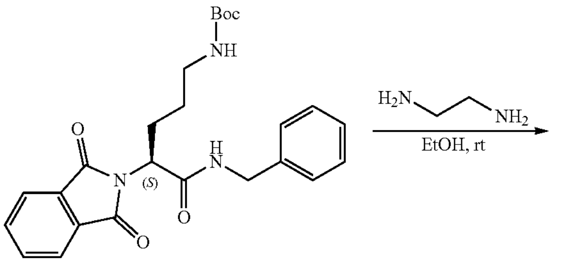

1-2

-continued

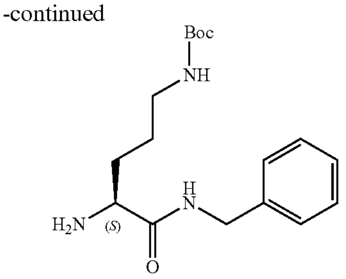

1-3

To a suspension of compound 1-2 (4.50 g, 9.97 mmol) in EtOH (100 mL) was added ethane-1,2-diamine (5.99 g, 99.6 mmol). The resulting solution was stirred at 70° C. for 1 hour. The mixture was concentrated under vacuum to afford crude product, which was purified by silica gel chromatography (elution gradient: DCM/MeOH, 20/1, v/v) to afford crude compound 1-3 (2.6 g) as a colorless oil, yield: 81%. The crude product was used directly without further purification.

Step 4:

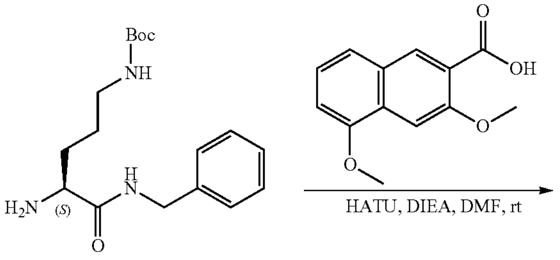

1-3

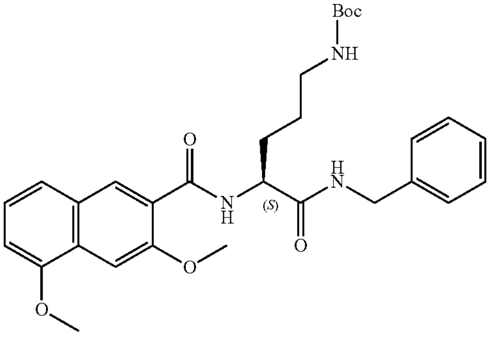

1-4

To a solution of compound 1-3 (2.60 g, 8.09 mmol), DIEA (1.64 mg, 16.1 mmol), HATU (4.61 g, 12.1 mmol) in DMF (50 mL) was added 3,5-dimethoxy-2-naphthoic acid (1.88 g, 8.09 mmol). The resulting solution was stirred at room temperature for 1 hour. The mixture was diluted with ethyl acetate (200 mL) and washed with water (50 mL×3), dried over anhydrous $Na_2SO_4$ and concentrated under vacuum to afford crude product, which was purified by silica gel chromatography (elution gradient: dichloromethane/methanol, 20/1, v/v) to afford compound 1-4 (3.5 g) as a yellow solid, yield: 80%. $^1H$ NMR (400 MHz, DMSO-$d_6$) δ ppm 1.37 (s, 9H), 1.42-1.53 (m, 2H), 1.63-1.85 (m, 2H), 2.90-2.97 (m, 2H), 3.99 (d, J=4.0 Hz, 6H), 4.34 — 4.36 (m, 2H), 4.56-4.59 (m, 2H), 6.84-6.87 (m, 1H), 7.04 (d, J=8.0 Hz, 1H), 7.23-7.37 (m, 6H), 7.54 — 7.57 (m, 2H), 8.34 (s, 1H), 8.53-8.61 (m, 2H). MS (ESI) m/z=535.7 [M+H]$^+$.

Step 5:

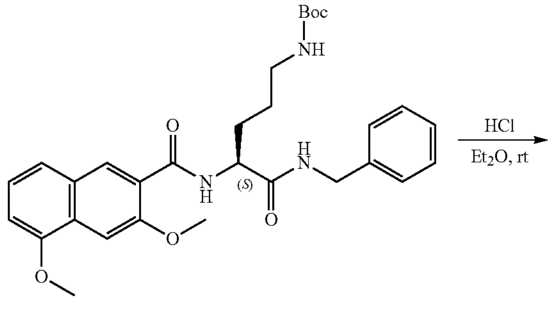

1-4

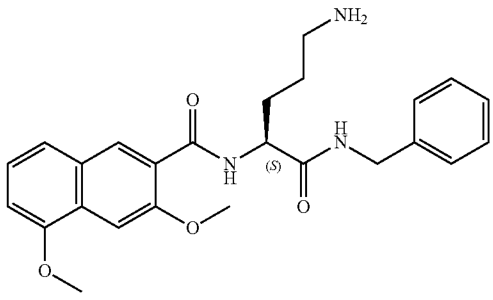

1-5

To a solution of compound 1-4 (3.50 g, 6.53 mmol) in diethyl ether (10 mL) was added hydrochloric acid solution (30 mL, 2N in diethyl ether). The mixture was stirred at room temperature for 3 hours. The precipitate was collected by filtration, washed with diethyl ether (20 mL) and dried under vacuum to afford compound 1-5 (3.0 g) as a yellow solid, yield: 97%. MS (ESI) m/z=435.7 [M+H]$^+$.

Step 6:

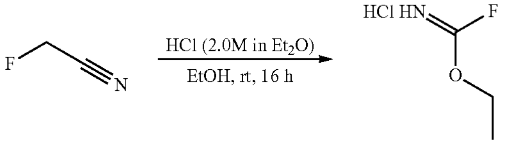

1-6

Into a 100-mL round-bottom flask, was placed hydrogen chloride (2.0 M in $Et_2O$, 60 mL, 120 mmol, 4.72 equiv.), 2-fluoroacetonitrile (1.5 g, 25 mmol, 1 equiv.) and ethanol (1.29 g, 27.9 mmol, 1.1 equiv.). The resulting solution was stirred for 16 hours at room temperature. The solids were collected by filtration and the solid was dried in an oven under reduced pressure. This resulted in 2.8 g (78%) of ethyl 2-fluoroethanimidate hydrochloride (1-6).

Step 7:

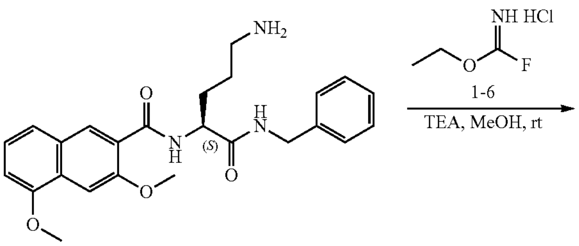

1-5

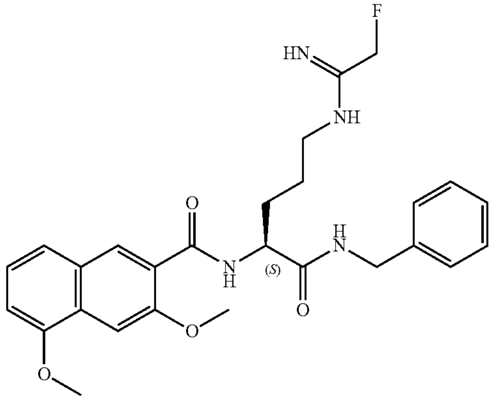

EX-1

To a solution of compound 1-5 (3.00 g, 6.36 mmol) and compound 1-6 (3.60 g, 25.4 mmol) in MeOH (20 mL) was added TEA (6.43 g, 63.5 mmol). The resulting mixture was stirred at room temperature for 3 hours. The mixture was quenched with 2N HCl and concentrated to give a residue, which was purified by preparative HPLC (Gemini-C18 column, 5 μ silica, 21 mm diameter, 150 mm length), using decreasingly polar mixtures of water (containing 0.1% formic acid) and MeCN as eluents (20-35%). Fractions containing the desired compound were concentrated and adjusted pH to 9-10 with 28% ammonium hydroxide aqueous solution and then extracted with ethyl acetate (50 mL×3). The organic phase was washed with water (50 mL), brine (50 mL) and concentrated under vacuum to give a residue. The residue was diluted with water (10 mL) and hydrochloric acid aqueous solution (5 mL, 1N) and lyophilized under vacuum to afford EX-1 (2.2 g, hydrochloric acid salt) as a yellow solid, yield: 70%. $^1$H NMR (400 MHz, DMSO-$d_6$): δ ppm 1.64-2.02 (m, 4H), 3.33-3.37 (m, 2H), 4.00 (d, J=1.6 Hz, 6H), 4.36 (d, J=5.6 Hz, 2H), 4.64-4.69 (m, 1H), 5.31 (d, J=45.2 Hz, 2H), 7.05 (d, J=7.6 Hz, 1H), 7.24-7.38 (m, 6H), 7.54-7.58 (m, 2H), 8.34 (s, 1H), 8.68-8.73 (m, 2H), 9.22 (s, 1H), 9.43 (s, 1H), 9.92 (s, 1H). MS (ESI) m/z =494.7 [M+H]$^+$.

The following compounds were prepared similarly to Example 1 using appropriate starting materials or reagents:

| COMPOUND | NAME | STRUCTURE | MS (ESI) m/z [M + H]+ |
| --- | --- | --- | --- |
| EX-2 | (S)-N-(1-(Benzylamino)-5-(2-fluoroacetimidamido)-1-oxopentan-2-yl)-3-methoxy-2-naphthamide | 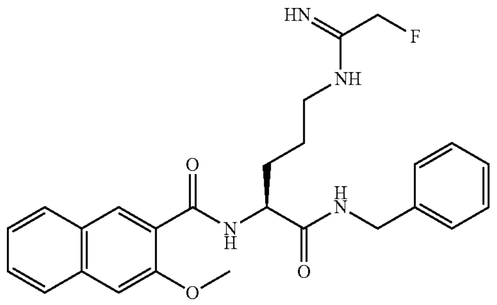 [SMILES: COc1cc2ccccc2cc1C(=O)N[C@@H](CCCNC(=N)CF)C(=O)NCc1ccccc1] | 465.2 |
| EX-3 | (S)-N-(1-((4-Chlorobenzyl)amino)-5-(2-fluoroacetimidamido)-1-oxopentan-2-yl)-2,6-dimethoxybenzamide | 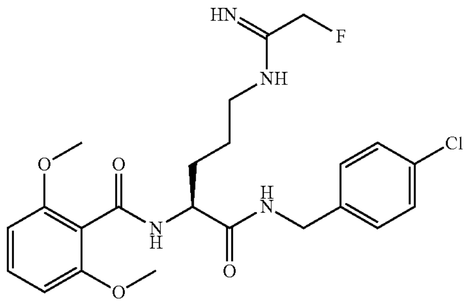 [SMILES: COc1cccc(OC)c1C(=O)N[C@@H](CCCNC(=N)CF)C(=O)NCc1ccc(Cl)cc1] | 479.1 |
| EX-4 | (S)-2-Chloro-N-(1-((4-chlorobenzyl)amino)-5-(2-fluoroacetimidamido)-1-oxopentan-2-yl)-6-methoxybenzamide | 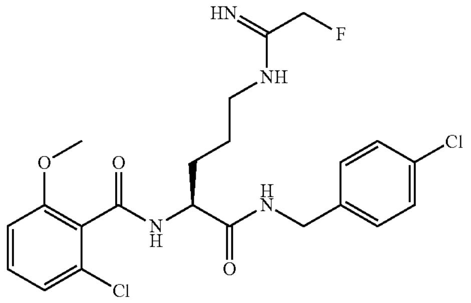 [SMILES: COc1cccc(Cl)c1C(=O)N[C@@H](CCCNC(=N)CF)C(=O)NCc1ccc(Cl)cc1] | 483.1 |
| EX-5 | (S)-N-(1-((4-Chlorobenzyl)amino)-5-(2-fluoroacetimidamido)-1-oxopentan-2-yl)-2-methoxybenzamide | 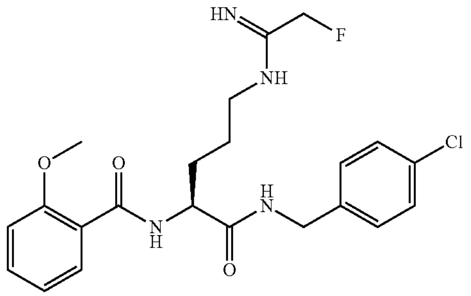 [SMILES: COc1ccccc1C(=O)N[C@@H](CCCNC(=N)CF)C(=O)NCc1ccc(Cl)cc1] | 449.2 |

-continued

| COM-POUND | NAME | STRUCTURE | MS (ESI) m/z [M + H]$^+$ |
|---|---|---|---|
| EX-6 | (S)-5-Chloro-N-(1-((4-chlorobenzyl)amino)-5-(2-fluoroacetimidamido)-1-oxopentan-2-yl)-2-methoxybenzamide | 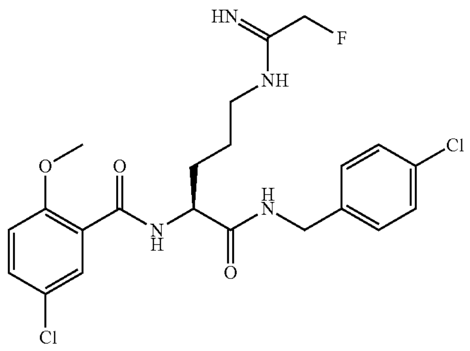 [SMILES: COc1ccc(Cl)cc1C(=O)N[C@@H](CCCNC(=N)CF)C(=O)NCc1ccc(Cl)cc1] | 483.1 |
| EX-7 | (S)-N-(1-(Benzylamino)-5-(2-fluoroacetimidamido)-1-oxopentan-2-yl)-4-methoxy-[1,1'-biphenyl]-3-carboxamide | 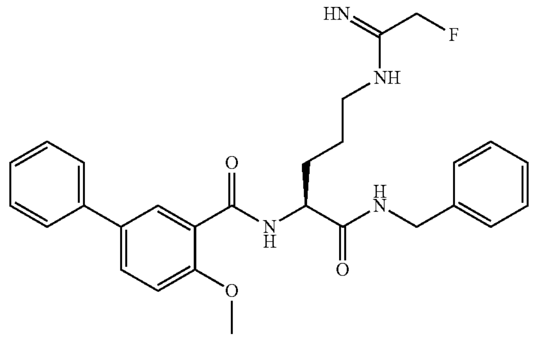 [SMILES: COc1ccc(-c2ccccc2)cc1C(=O)N[C@@H](CCCNC(=N)CF)C(=O)NCc1ccccc1] | 491.3 |
| EX-8 | (S)-N-(5-(2-Fluoroacetimidamido)-1-((3-methylbenzyl)amino)-1-oxopentan-2-yl)-4-methoxy-[1,1'-biphenyl]-3-carboxamide | 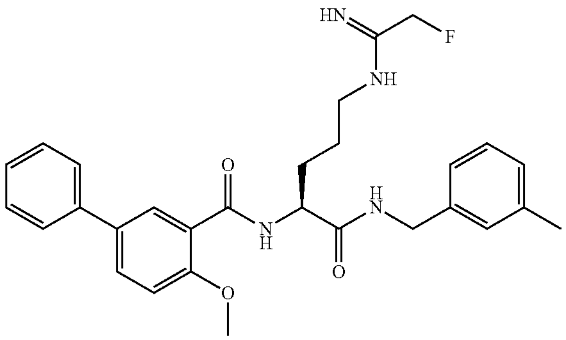 [SMILES: COc1ccc(-c2ccccc2)cc1C(=O)N[C@@H](CCCNC(=N)CF)C(=O)NCc1cccc(C)c1] | 505.3 |
| EX-9 | (S)-N-(1-((3-Chlorobenzyl)amino)-5-(2-fluoroacetimidamido)-1-oxopentan-2-yl)-4-methoxy-[1,1'-biphenyl]-3-carboxamide | 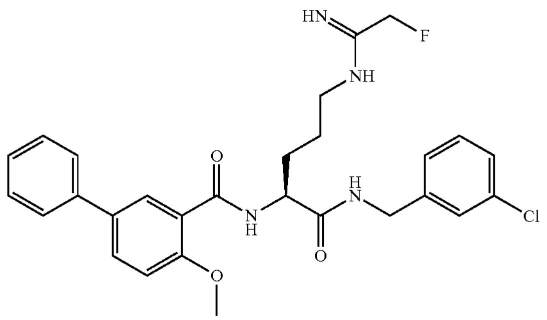 [SMILES: COc1ccc(-c2ccccc2)cc1C(=O)N[C@@H](CCCNC(=N)CF)C(=O)NCc1cccc(Cl)c1] | 525.3 |

-continued

| COMPOUND | NAME | STRUCTURE | MS (ESI) m/z [M + H]+ |
|---|---|---|---|
| EX-10 | (S)-N-(5-(2-Fluoroacetimidamido)-1-oxo-1-((pyridin-2-ylmethyl)amino)pentan-2-yl)-4-methoxy-[1,1'-biphenyl]-3-carboxamide | 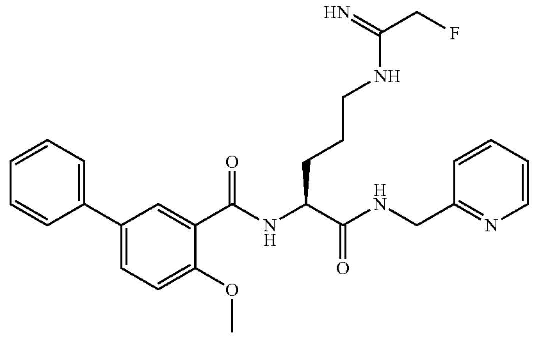 [SMILES: COc1ccc(-c2ccccc2)cc1C(=O)N[C@@H](CCCNC(=N)CF)C(=O)NCc1ccccn1] | 492.3 |
| EX-11 | (S)-N-(1-(Benzylamino)-5-(2-fluoroacetimidamido)-1-oxopentan-2-yl)-3'-chloro-4-methoxy-[1,1'-biphenyl]-3-carboxamide | 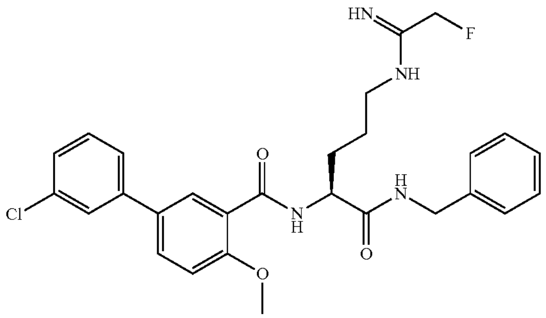 [SMILES: COc1ccc(-c2cccc(Cl)c2)cc1C(=O)N[C@@H](CCCNC(=N)CF)C(=O)NCc1ccccc1] | 525.3 |
| EX-12 | (S)-N-(1-(Benzylamino)-5-(2-fluoroacetimidamido)-1-oxopentan-2-yl)-4-methoxy-3'-methyl-[1,1'-biphenyl]-3-carboxamide | 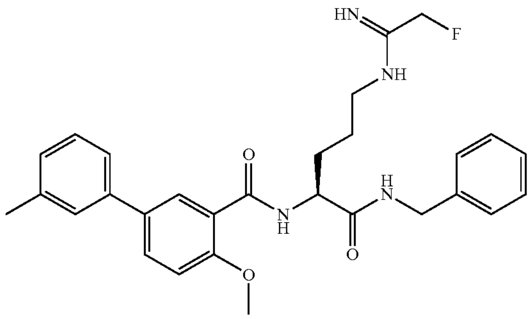 [SMILES: COc1ccc(-c2cccc(C)c2)cc1C(=O)N[C@@H](CCCNC(=N)CF)C(=O)NCc1ccccc1] | 505.3 |
| EX-13 | (S)-N-(5-(2-Fluoroacetimidamido)-1-((2-methoxybenzyl)amino)-1-oxopentan-2-yl)-4-methoxy-[1,1'-biphenyl]-3-carboxamide | 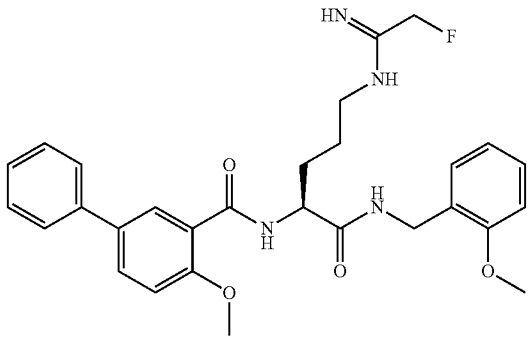 [SMILES: COc1ccccc1CNC(=O)[C@H](CCCNC(=N)CF)NC(=O)c1cc(-c2ccccc2)ccc1OC] | 521.3 |

-continued

| COMPOUND | NAME | STRUCTURE | MS (ESI) m/z $[M + H]^+$ |
|---|---|---|---|
| EX-14 | (S)-5-Chloro-N-(1-((3-chlorobenzyl)amino)-5-(2-fluoroacetimidamido)-1-oxopentan-2-yl)-2-methoxybenzamide | 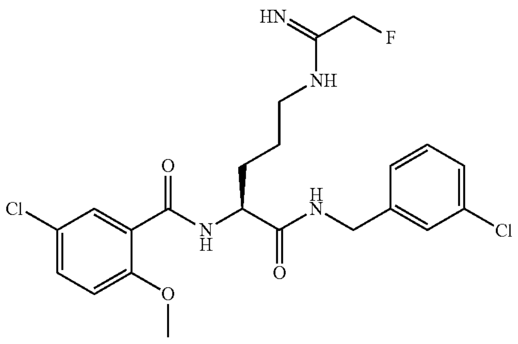 [SMILES: COc1ccc(Cl)cc1C(=O)N[C@@H](CCCNC(=N)CF)C(=O)NCc1cccc(Cl)c1] | 483.2 |
| EX-15 | (S)-5-Chloro-N-(1-((2-chlorobenzyl)amino)-5-(2-fluoroacetimidamido)-1-oxopentan-2-yl)-2-methoxybenzamide | 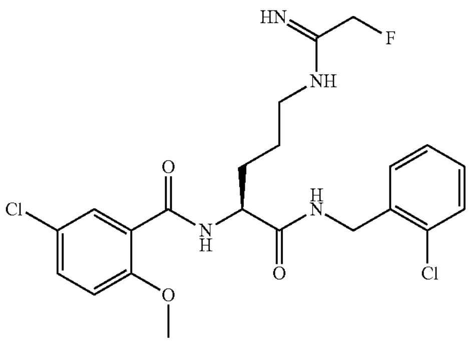 [SMILES: COc1ccc(Cl)cc1C(=O)N[C@@H](CCCNC(=N)CF)C(=O)NCc1ccccc1Cl] | 483.2 |
| EX-16 | (S)-5-Chloro-N-(5-(2-fluoroacetimidamido)-1-((4-methylbenzyl)amino)-1-oxopentan-2-yl)-2-methoxybenzamide | 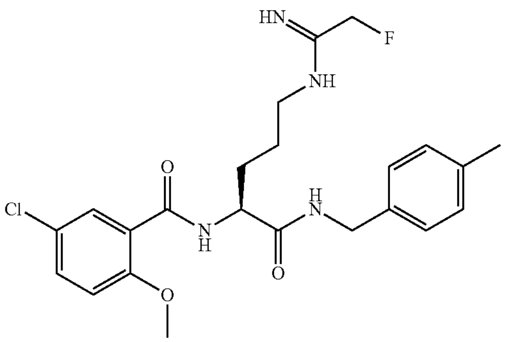 [SMILES: COc1ccc(Cl)cc1C(=O)N[C@@H](CCCNC(=N)CF)C(=O)NCc1ccc(C)cc1] | 463.3 |
| EX-17 | (S)-5-Chloro-N-(5-(2-fluoroacetimidamido)-1-((4-methoxybenzyl)amino)-1-oxopentan-2-yl)-2-methoxybenzamide | 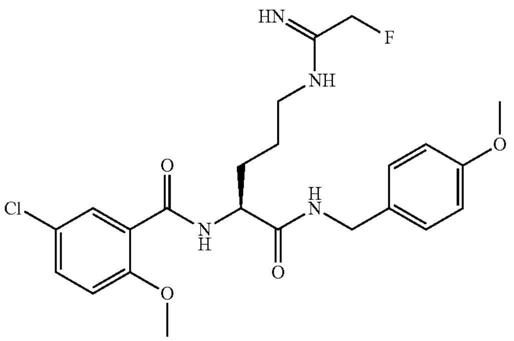 [SMILES: COc1ccc(CNC(=O)[C@H](CCCNC(=N)CF)NC(=O)c2cc(Cl)ccc2OC)cc1] | 479.3 |

-continued

| COMPOUND | NAME | STRUCTURE | MS (ESI) m/z [M + H]+ |
|---|---|---|---|
| EX-18 | (S)-5-Chloro-N-(5-(2-fluoroacetimidamido)-1-oxo-1-((pyridin-2-ylmethyl)amino)pentan-2-yl)-2-methoxybenzamide | 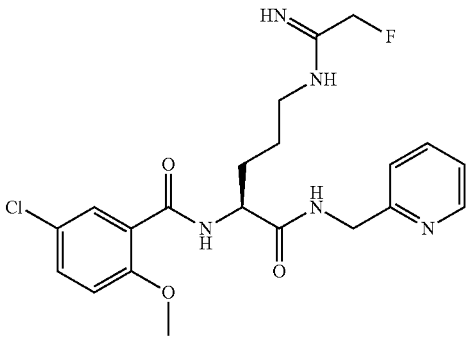 [SMILES: COc1ccc(Cl)cc1C(=O)N[C@@H](CCCNC(=N)CF)C(=O)NCc1ccccn1] | 450.3 |
| EX-19 | (S)-N-(1-((4-Chlorobenzyl)amino)-5-(2-fluoroacetimidamido)-1-oxopentan-2-yl)-3,5-dimethoxy-2-naphthamide | 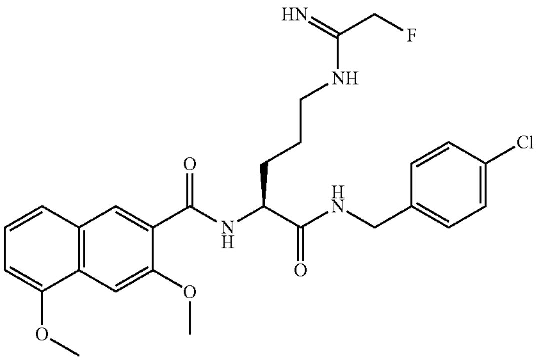 [SMILES: COc1cc2c(OC)cccc2cc1C(=O)N[C@@H](CCCNC(=N)CF)C(=O)NCc1ccc(Cl)cc1] | 529.3 |
| EX-20 | (S)-N-(1-((3-Chlorobenzyl)amino)-5-(2-fluoroacetimidamido)-1-oxopentan-2-yl)-3,5-dimethoxy-2-naphthamide | 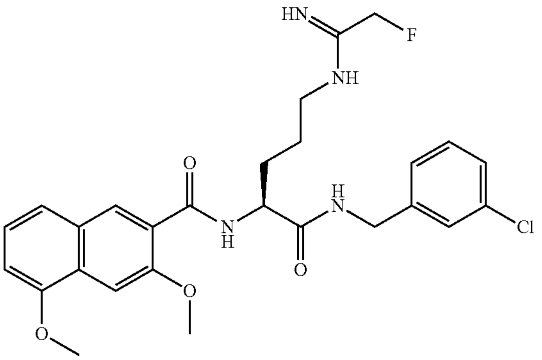 [SMILES: COc1cc2c(OC)cccc2cc1C(=O)N[C@@H](CCCNC(=N)CF)C(=O)NCc1cccc(Cl)c1] | 529.3 |
| EX-21 | (S)-N-(5-(2-Fluoroacetimidamido)-1-((3-fluorobenzyl)amino)-1-oxopentan-2-yl)-3,5-dimethoxy-2-naphthamide | 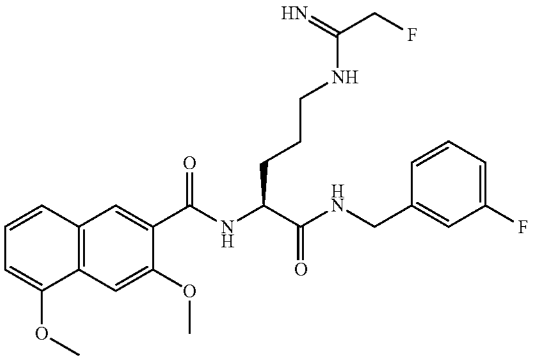 [SMILES: COc1cc2c(OC)cccc2cc1C(=O)N[C@@H](CCCNC(=N)CF)C(=O)NCc1cccc(F)c1] | 513.3 |

-continued

| COM-POUND | NAME | STRUCTURE | MS (ESI) m/z $[M + H]^+$ |
|---|---|---|---|
| EX-22 | (S)-N-(5-(2-Fluoroacetimidamido)-1-((4-fluorobenzyl)amino)-1-oxopentan-2-yl)-3,5-dimethoxy-2-naphthamide | 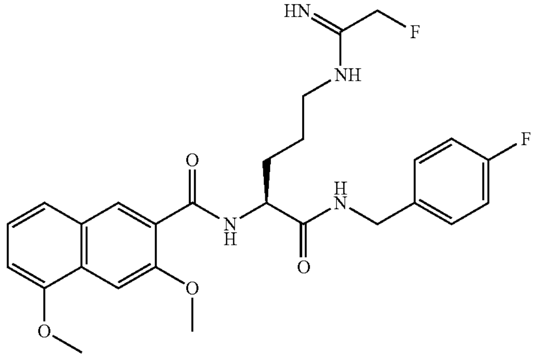 [SMILES: COc1cc2c(OC)cccc2cc1C(=O)N[C@@H](CCCNC(=N)CF)C(=O)NCc1ccc(F)cc1] | 513.3 |
| EX-23 | (S)-N-(1-(Benzylamino)-5-(2-fluoroacetimidamido)-1-oxopentan-2-yl)-6-(dimethylamino)-1-methoxy-2-naphthamide | 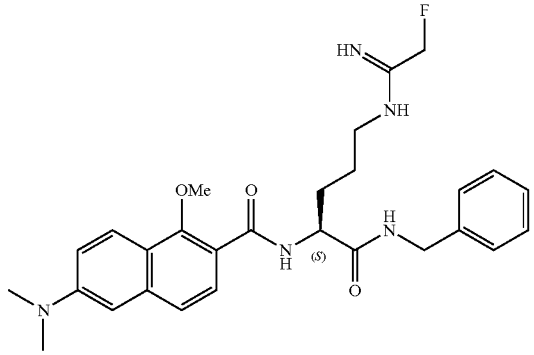 | 508.2 |

Example 2

Synthesis of N-((S)-5-(2-fluoroacetimidamido)-1-oxo-1-43-(4-(5-((3aS,4S,6aR)-2-oxohexahydro-1H-thieno[3,4-d]imidazol-4-yl)pentanamido)butanamido)benzyl)amino)pentan-2-yl)-3,5-dimethoxy-2-naphthamide (EX-24)

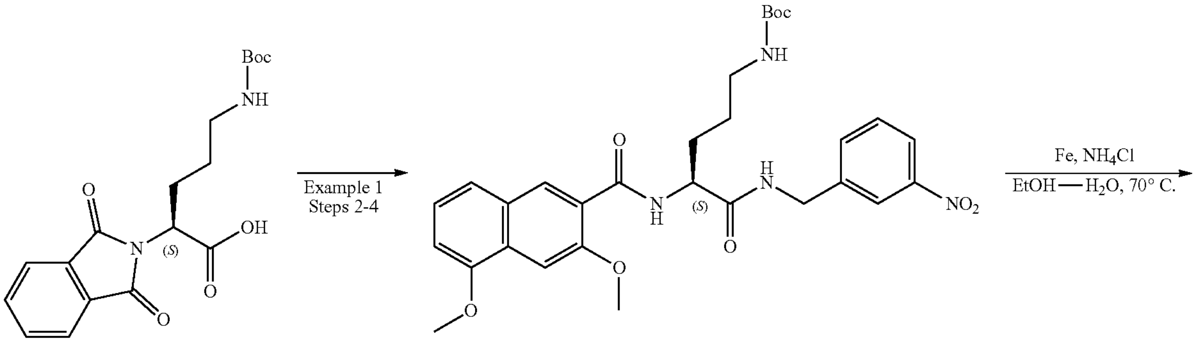

1-1 2-1

-continued
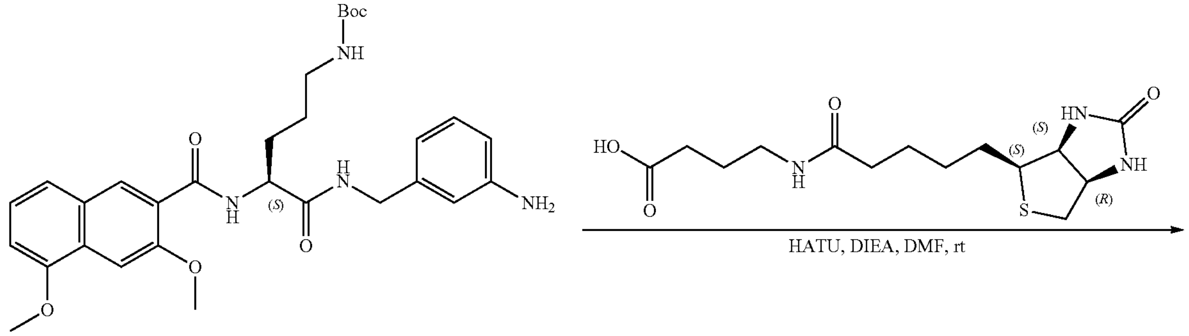
2-2
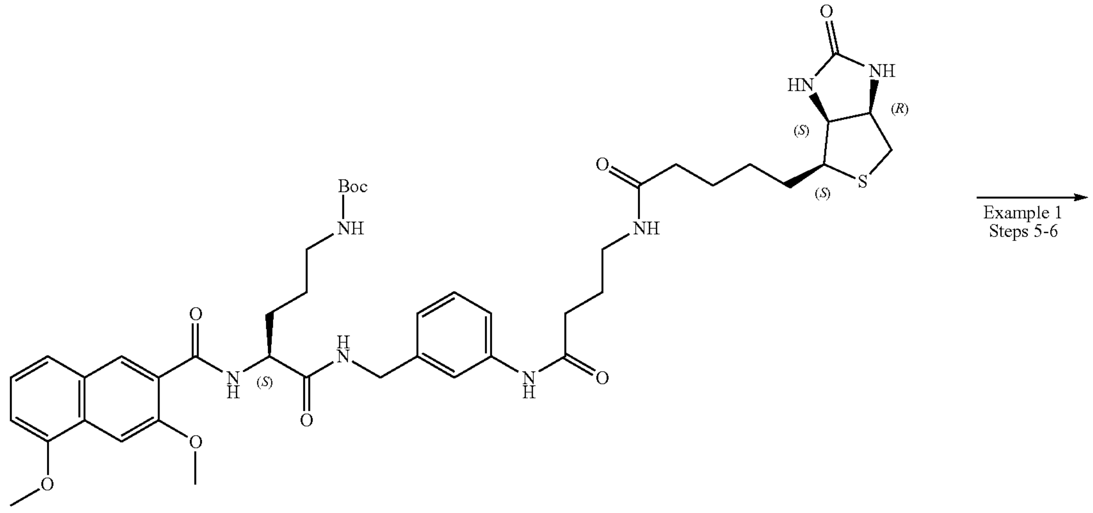
2-3
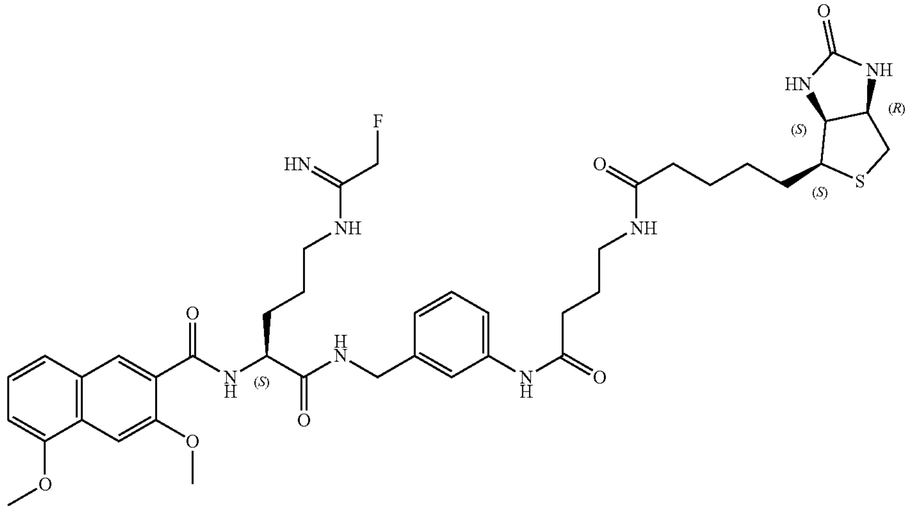
EX-24

Step 1:
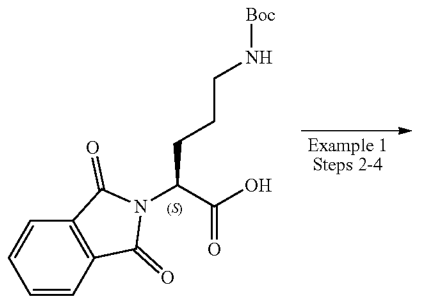
1-1
-continued
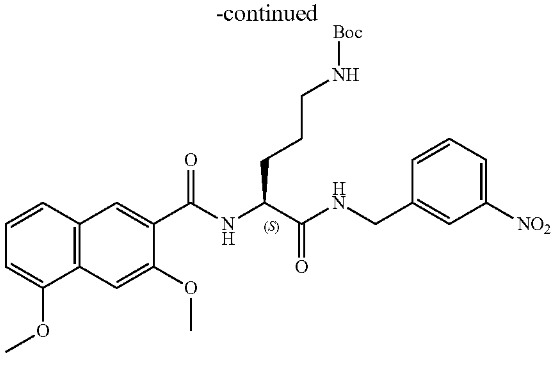
2-1
Compound 2-1 was prepared from compound 1-1 similarly to Example 1, Steps 2-4, using appropriate chemicals and reagents. MS (ESI) m/z =580.7 $[M+H]^+$.
Step 2:
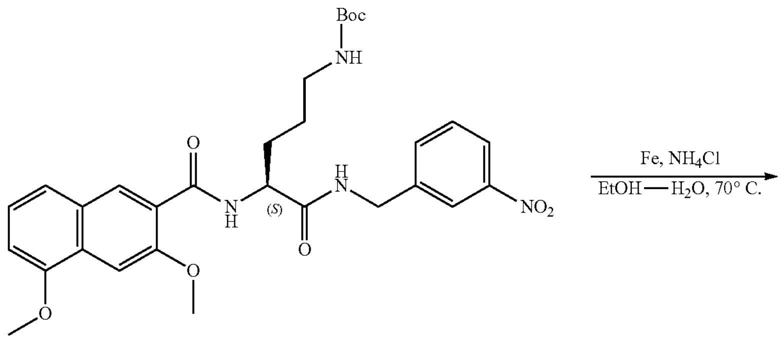
2-1
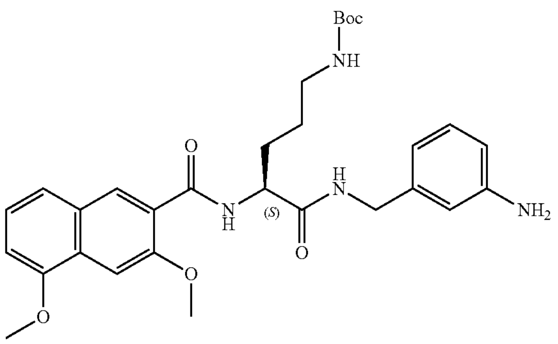
2-2

To a solution of compound 2-1 (400 mg, 0.68 mmol) in ethanol (20 mL) and water (2 mL) was added iron powder (192 mg, 3.44 mmol) and $NH_4Cl$ (184 mg, 3.44 mmol). The mixture was stirred at 70° C. for 3 hours. The mixture was filtered and the filtrate was concentrated under vacuum. The residue was diluted with ethyl acetate (50 mL), washed with water (30 mL) and brine (30 mL), dried over anhydrous $Na_2SO_4$ and concentrated under vacuum to afford crude a product which was purified by silica gel chromatography (DCM/MeOH, 10/1, v/v) to afford compound 7 (320 mg) as a brown solid, yield: 85.3%. $^1H$ NMR (400 MHz, MeOD) δ ppm 8.35 (s, 1H), 7.67 (s, 1H), 7.48-7.40 (m, 1H), 7.32 (t, J=8.0 Hz, 1H), 7.13-6.91 (m, 2H), 6.75-6.53 (m, 3H), 4.72-4.65 (m, 1H), 4.40-4.30 (m, 2H), 4.07-3.95 (m, 6H), 3.18-2.95 (m, 2H), 1.99-1.73 (m, 2H), 1.65-1.53 (m, 2H), 1.40 (s, 9H). MS (ESI) m/z=550.7 $[M+H]^+$.

Step 3:

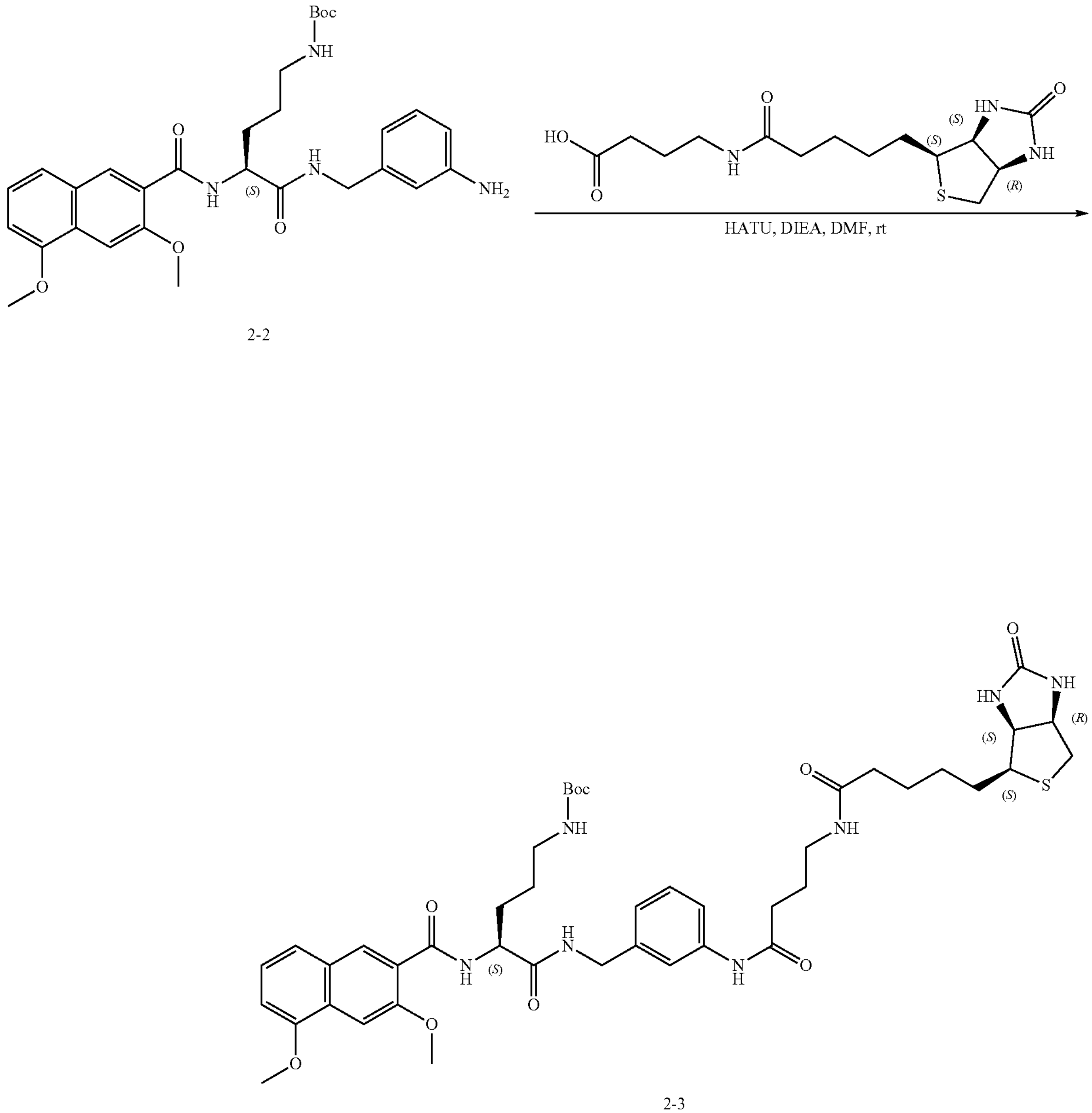

2-2

2-3

To a solution of compound 2-2 (320 mg, 0.58 mmol), DIEA (188 mg, 1.45 mmol), and HATU (264 mg, 0.7 mmol) in DMF (15 mL) was added 4-(5-((3aS,4S,6aR)-2-oxohexahydro-1H-thieno[3,4-d]imidazol-4-yl)pentanamido)butanoic acid (191 mg, 0.58 mmol). The resulting solution was stirred at room temperature for 16 hours. The mixture was diluted with ethyl acetate (50 mL), washed with water (30 mL×2) and brine (30 mL), dried over anhydrous $Na_2SO_4$ and concentrated under vacuum to afford a crude product which was purified by silica gel chromatography (DCM/MeOH, 10/1, v/v) to afford compound 2-3 (400 mg) as a brown solid, yield: 79.3%. MS (ESI) m/z=861.5 $[M+H]^+$.

Step 4:

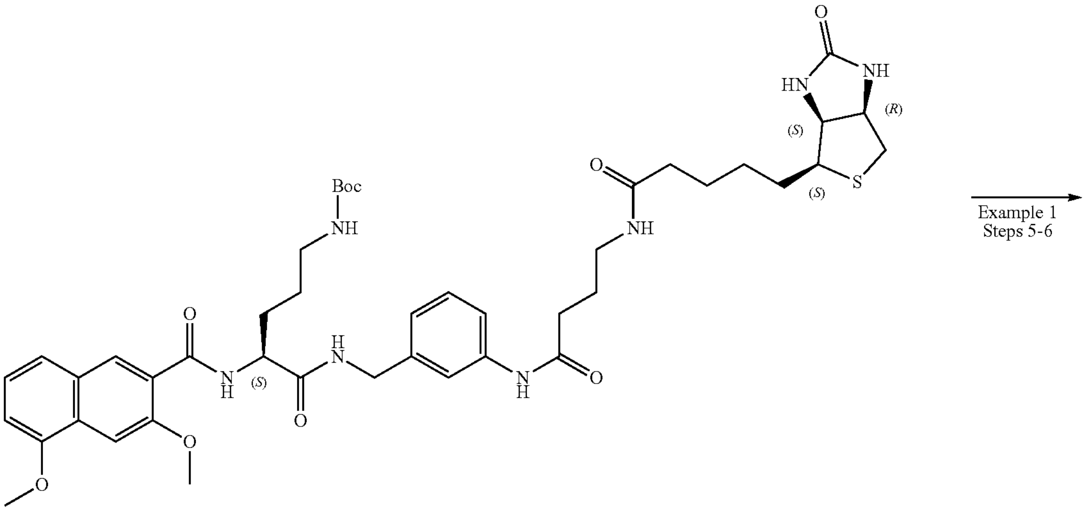

2-3

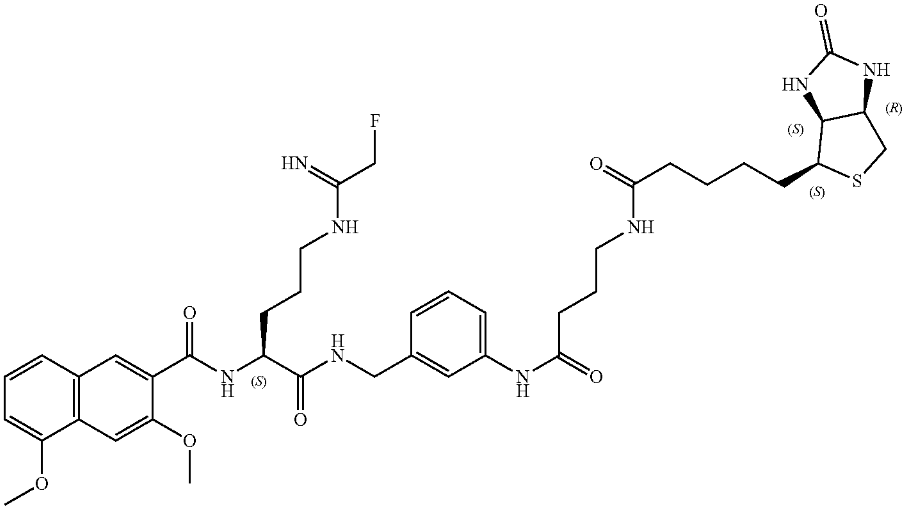

EX-24

Compound EX-24 was prepared from compound 2-3 similarly to Example 1, Steps-5-6, as a hydrochloride salt. $^1H$ NMR (400 MHz, DMSO-$d_6$) δ ppm 10.10 (s, 1H), 9.96 (s, 1H), 9.45 (s, 1H), 9.25 (s, 1H), 8.85-8.61 (m, 2H), 8.35 (s, 1H), 7.93 (s, 1H), 7.62-7.45 (m, 4H), 7.39-7.21 (m, 2H), 7.07-6.92(m, 2H), 5.42-5.15(m, 2H), 4.66 (s, 1H), 4.40-4.22 (m, 3H), 4.15-4.07 (m, 1H), 3.99 (s, 6H), 3.45-3.25 (m, 2H), 3.15-2.96(m, 3H), 2.90-2.75 (m, 1H), 2.36-2.25 (m, 2H), 2.11-2.02 (m, 2H), 1.82-1.26 (m, 13H). MS (ESI) m/z=820.5 $[M+H]^+$.

Example 3

PAD4 Inhibition Assay

PAD4 was diluted to 75 nM in Assay Buffer (50 mM Tris-HCl, 2 mM $CaCl_2$, 2 mM DTT, 1 mM PMSF in $H_2O$) and added to wells with various concentrations of compound or DMSO vehicle in Eppendorf tubes (final volume was 100 μL). Following a 60-minute preincubation at 37° C., the reaction was initiated by the addition of 10 μL substrate (22 mM BAEE in $H_2O$) at 37° C. The reaction was stopped after 90 minutes by the addition of 25 μL $HClO_4$ (5 M), 125 μL Reagent A (10 g/L diacetyl monoxime and 15 g/L NaCl in $H_2O$) and 250 μL Reagent B (10 mg/mL antipyrine and 1.5 mg/mL $FeCl_3$ diluted in detection buffer containing 25% $H_2SO_4$, 25% $H_3PO_4$ and 50% $H_2O$) in sequence. This assay was quenched in an ice-bath for 5 minutes after boiling for 30 minutes. The citrulline formation was measured in fluorescence (λ=465 nm) on microplate reader and the $IC_{50}$ was calculated by GraphPad Prism 5.

The resulting $IC_{50}$ values are provided in Table 1 below.

TABLE 1

$IC_{50}$ values.

| EXAMPLE | $IC_{50}$[a] |
|---|---|
| EX-1 | ** |
| EX-2 | ** |
| EX-3 | ** |
| EX-4 | * |
| EX-5 | * |
| EX-6 | ** |
| EX-7 | ** |
| EX-8 | * |
| EX-9 | * |
| EX-10 | ** |
| EX-11 | * |
| EX-12 | ** |
| EX-13 | ** |
| EX-14 | ** |
| EX-15 | ** |
| EX-16 | ** |
| EX-17 | ** |
| EX-18 | ** |
| EX-19 | ** |
| EX-20 | ** |
| EX-21 | ** |
| EX-22 | ** |
| EX-23 | ** |
| EX-24 | ** |

[a]** <0.5 μM; * 0.5-10 μM.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A compound of formula (I):

(I)

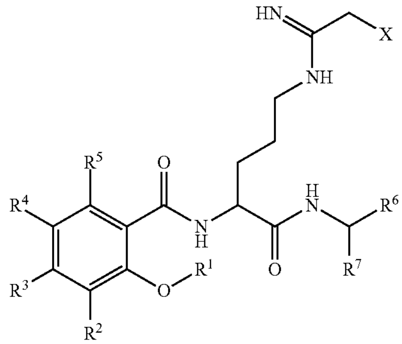

or a pharmaceutically acceptable salt, prodrug, or metabolite thereof, or a solvate or hydrate of any of the foregoing, wherein, X is halogen;

$R^1$ is selected from the group consisting of optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl;

each of $R^2$, $R^3$, $R^4$ and $R^5$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, or $R^2$ and $R^3$ combined with the atoms to which they are attached form an optionally substituted ring A1, said ring A1 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A1 is unsubstituted or independently substituted with one or more $R^{9a}$;

or $R^3$ and $R^4$ combined with the atoms to which they are attached form an optionally substituted ring A2, said ring A2 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A2 is unsubstituted or independently substituted with one or more $R^{9b}$;

or $R^4$ and $R^5$ combined with the atoms to which they are attached form an optionally substituted ring A3, said ring A3 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl, said ring A3 is unsubstituted or independently substituted with one or more $R^{9c}$;

each of $R^6$ and $R^7$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino, each of $R^{9a}$, $R^{9b}$ and $R^{9c}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

2. The compound of claim 1, wherein X is selected from the group consisting of F and Cl.

3. The compound of claim 1 wherein $R^1$is optionally substituted ($C_1$-$C_8$) alkyl.

4. The compound of claim 1 wherein $R^1$is optionally substituted methyl.

5. The compound of claim 1 wherein $R^2$ is hydrogen, and/or $R^3$ is hydrogen.

6. The compound of claim 1, wherein $R^4$ is selected from the group consisting of hydrogen, halogen, and optionally substituted ($C_6$-$C_{10}$) aryl.

7. The compound of claim 1, wherein $R^4$ is selected from the group consisting of F, Cl, and optionally substituted phenyl.

8. The compound of claim 1, wherein $R^4$ is substituted with one or more $R^8$, each $R^8$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

9. The compound of claim 8, wherein $R^8$ is selected from the group consisting of hydrogen, halogen, and optionally substituted ($C_1$-$C_8$) alkyl.

10. The compound of claim 8, wherein $R^8$ is selected from the group consisting of F, Cl, and optionally substituted phenyl.

11. The compound of claim 1, wherein $R^2$ and $R^3$ combined with the atoms to which they are attached form an optionally substituted ring A1, said ring A1 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

12. The compound of claim 1, wherein ring A1 is optionally substituted ($C_6$-$C_{10}$) aryl.

13. The compound of claim 1, wherein ring A1 is optionally substituted phenyl.

14. The compound of claim 1, wherein ring A1 is substituted with one or more $R^{9a}$, each $R^{9a}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

15. The compound of claim 1, wherein $R^{9a}$ is selected from the group consisting of hydrogen, optionally substituted ($C_1$-$C_8$) alkoxy, and optionally substituted ($C_1$-$C_8$) alkylamino.

16. The compound of claim 1, wherein $R^{9a}$ is optionally substituted N, N-dimethylamino.

17. The compound of claim 1, wherein $R^3$ and $R^4$ combined with the atoms to which they are attached form an optionally substituted ring A2, said ring A2 is selected from the group consisting of optionally substituted ($C_3$-$C_{10}$) carbocycle, optionally substituted ($C_2$-$C_9$) heterocycle, optionally substituted ($C_6$-$C_{10}$) aryl, and optionally substituted ($C_1$-$C_9$) heteroaryl.

18. The compound of claim 1, wherein ring A2 is optionally substituted ($C_6$-$C_{10}$) aryl.

19. The compound of claim 1, wherein ring A2 is optionally substituted phenyl.

20. The compound of claim 1, wherein ring A2 is substituted with one or more $R^{9b}$, each $R^{9b}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy and optionally substituted ($C_1$-$C_8$) alkylamino.

21. The compound of claim 1, wherein $R^{9b}$ is selected from the group consisting of hydrogen, optionally substituted ($C_1$-$C_8$) alkoxy, and optionally substituted ($C_1$-$C_8$) alkylamino.

22. The compound of claim 1, wherein $R^{9b}$ is optionally substituted methoxy.

23. The compound of claim 1, wherein $R^5$ is selected from the group consisting of hydrogen, halogen, and optionally substituted ($C_1$-$C_8$) alkoxy.

24. The compound of claim 1, wherein $R^5$ is selected from the group consisting of hydrogen, halogen, and optionally substituted methoxy.

25. The compound of claim 1, wherein $R^5$ is selected from the group consisting of F, Cl, and optionally substituted phenyl.

26. The compound of claim 1, wherein at least one of $R^6$ and $R^7$ is not hydrogen.

27. The compound of claim 1, wherein $R^6$ is selected from the group consisting of optionally substituted ($C_6$-$C_{10}$) aryl, and optionally substituted ($C_1$-$C_9$) heteroaryl.

28. The compound of claim 1, wherein $R^6$ is optionally substituted phenyl or optionally substituted pyridyl.

29. The compound of claim 1, wherein $R^6$ is substituted with one or more $R^{10}$, each $R^{10}$ is independently selected from the group consisting of hydrogen, halogen, optionally substituted ($C_1$-$C_8$) alkyl, optionally substituted ($C_2$-$C_8$) alkenyl, optionally substituted ($C_2$-$C_8$) alkynyl, optionally substituted ($C_1$-$C_8$) haloalkyl, optionally substituted ($C_3$-$C_{10}$) carbocycle, optionally substituted ($C_2$-$C_9$) heterocycle, optionally substituted ($C_6$-$C_{10}$) aryl, optionally substituted ($C_1$-$C_9$) heteroaryl, optionally substituted ($C_1$-$C_8$) alkoxy, optionally substituted ($C_1$-$C_8$) alkylamino and optionally substituted group

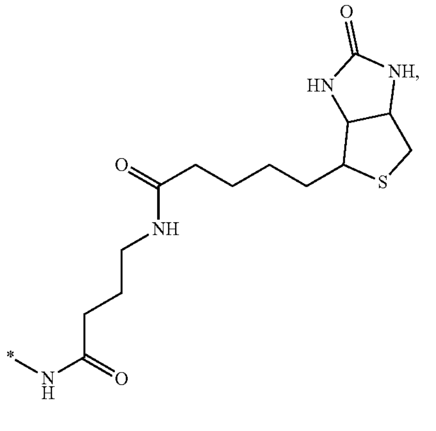 [SMILES: *NC(=O)CCCNC(=O)CCCCC1SCC2NC(=O)NC21]

wherein the asterisk "*" in the structure formulas indicates the available radical ends to be connected.

30. The compound of claim 1, wherein $R^6$ is substituted with one or more $R^{10}$, each $R^{10}$ is independently selected from the group consisting of hydrogen, halogen, optionally substituted ($C_1$-$C_8$) alkyl, optionally substituted ($C_1$-$C_8$) alkoxy and optionally substituted group

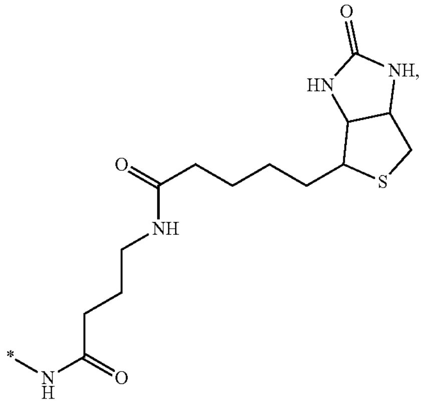 [SMILES: *NC(=O)CCCNC(=O)CCCCC1SCC2NC(=O)NC21]

wherein the asterisk "*" in the structure formulas indicates the available radical ends to be connected.

31. The compound of claim 26, wherein $R^{10}$ is selected from the group consisting of F, Cl, optionally substituted methyl, optionally substituted methoxy, and optionally substituted group

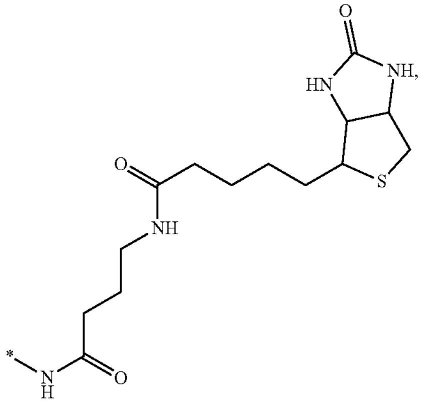 [SMILES: *NC(=O)CCCNC(=O)CCCCC1SCC2NC(=O)NC21]

wherein the asterisk "*" in the structure formulas indicates the available radical ends to be connected.

32. The compound of claim 1, which is of formula (II):

(II)

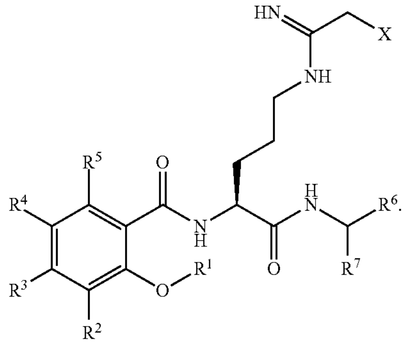

33. The compound of claim 1 or a pharmaceutically acceptable salt, prodrug, or metabolite thereof, or a solvate or hydrate of any of the foregoing, wherein, said compound is selected from the group consisting of:

EX-1

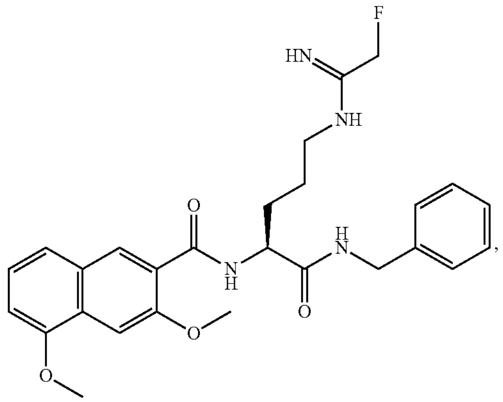

EX-2

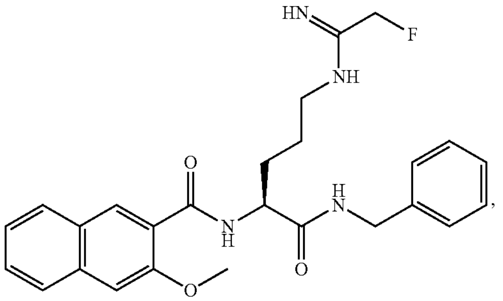

-continued
EX-3
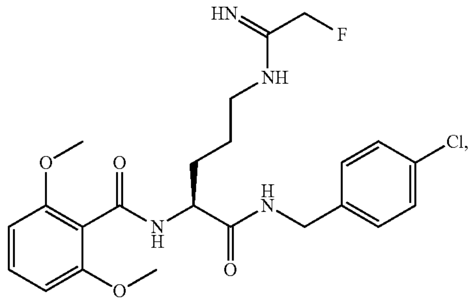
EX-4
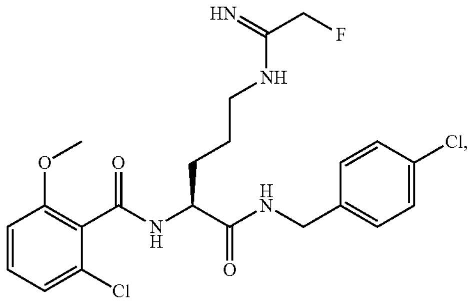
EX-5
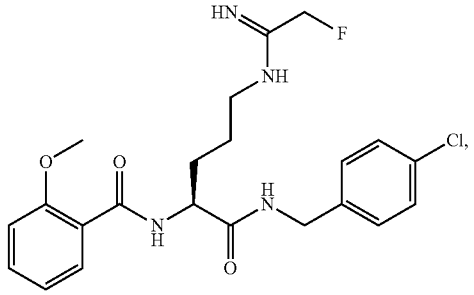
EX-6
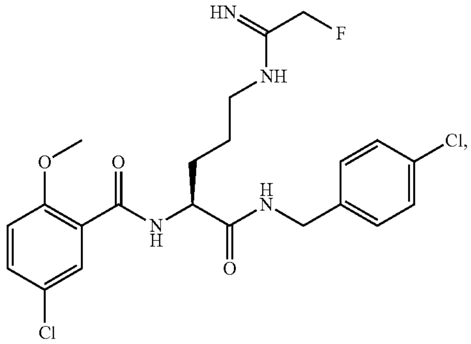
EX-7
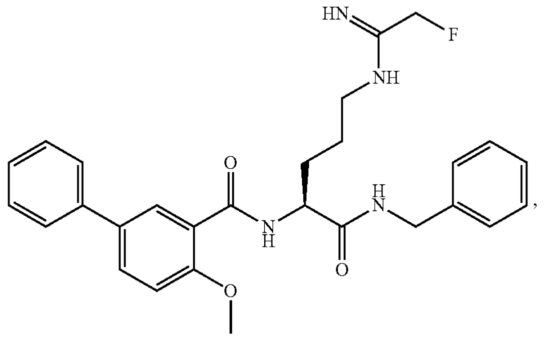
EX-8
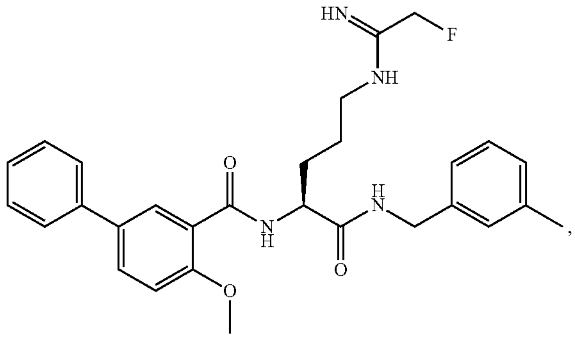
EX-9
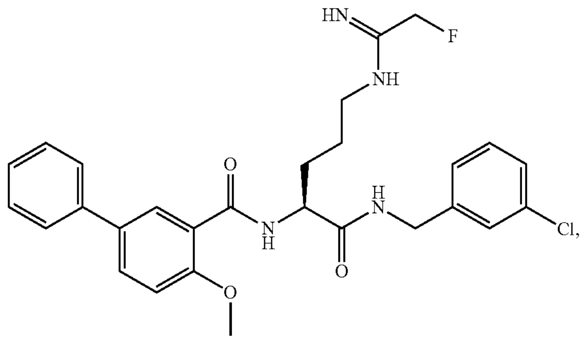
EX-10
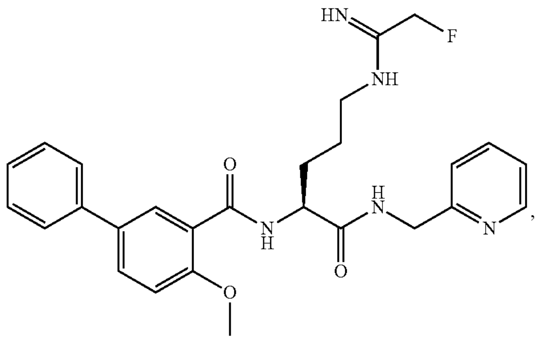

-continued
EX-11
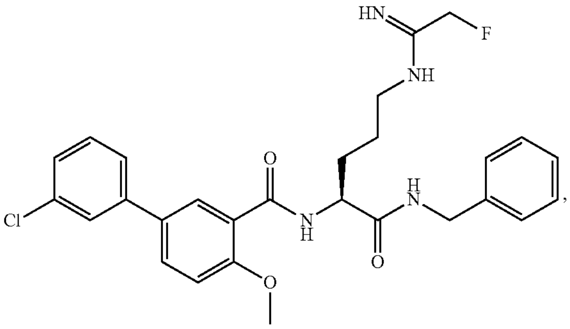,
EX-12
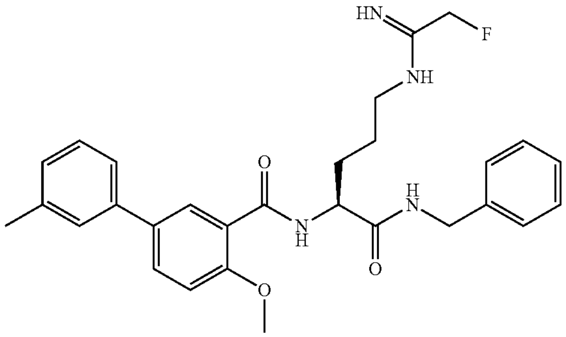,
EX-13
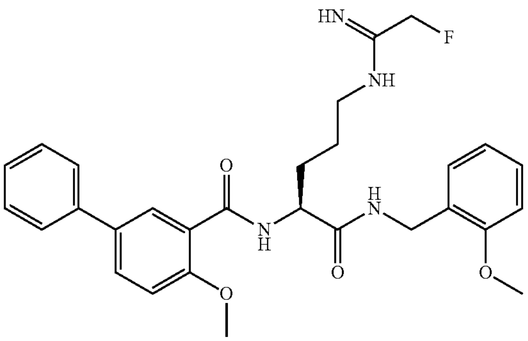,
EX-14
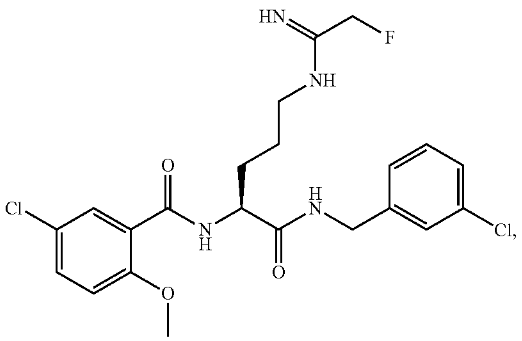,
EX-15
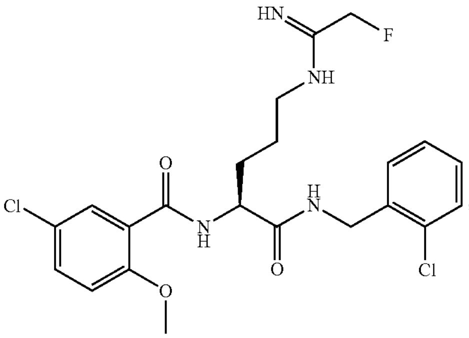,
EX-16
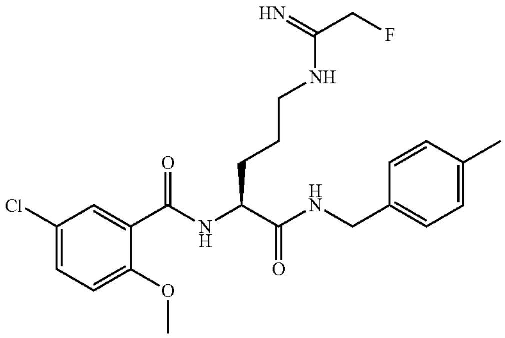,
EX-17
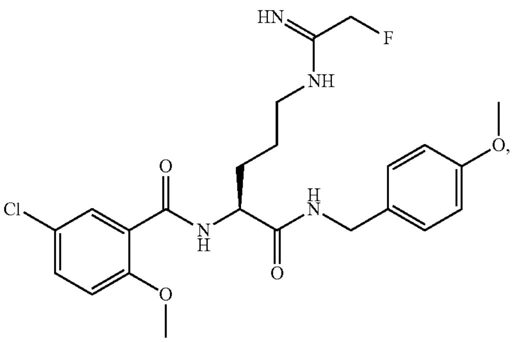,
EX-18
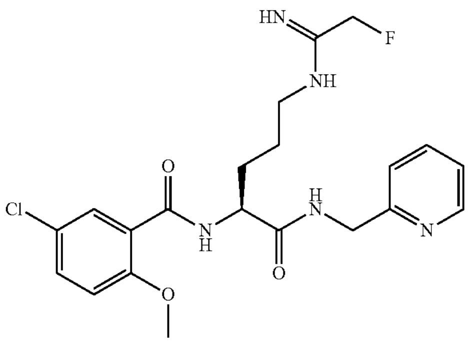, -continued
EX-19
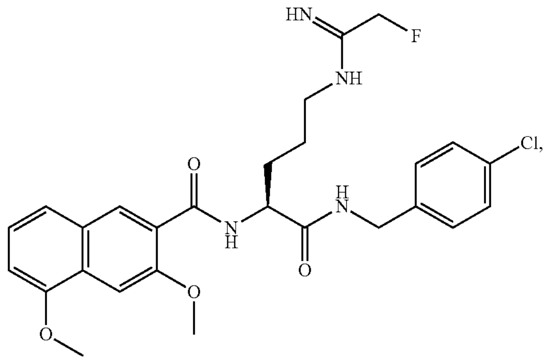
Cl,
EX-20
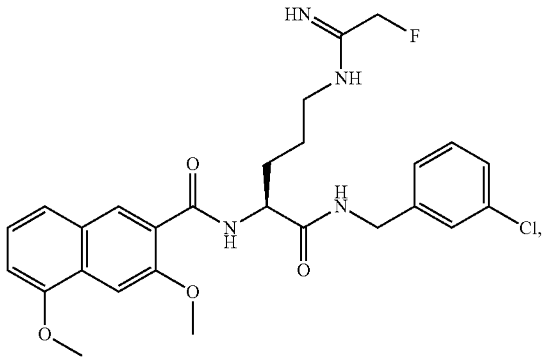
Cl,
EX-21
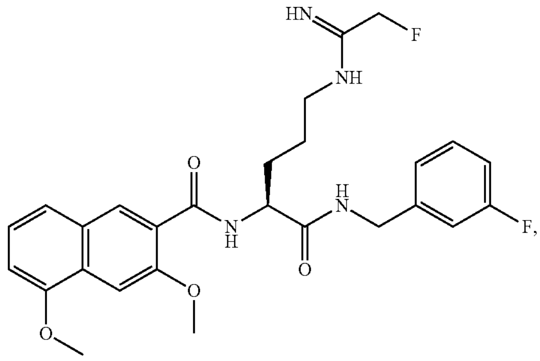
F,
EX-22
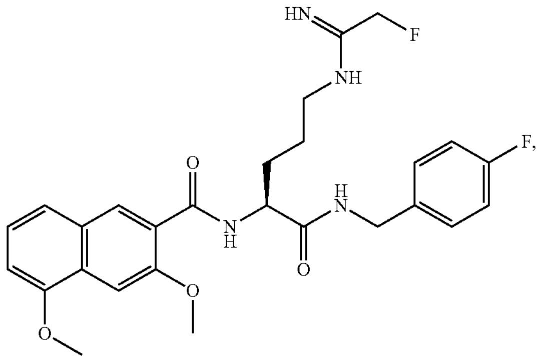
F,
EX-23
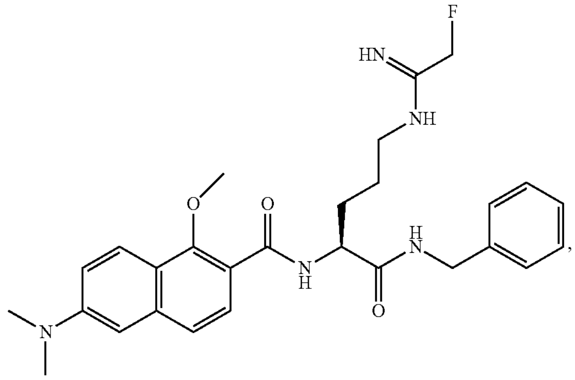
, and -continued

EX-24

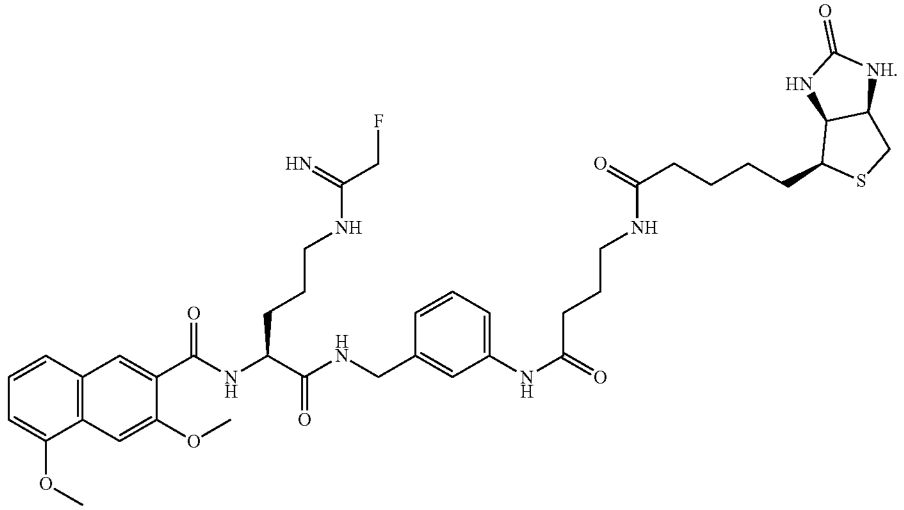

34. A composition comprising the compound of claim 1, or a pharmaceutically acceptable salt, prodrug, or metabolite thereof, or a solvate or hydrate of any of the foregoing, and optionally a pharmaceutically acceptable carrier.

35. The composition of claim 34, wherein said pharmaceutically acceptable salt is a hydrochloride salt.

36. The composition of claim 34, wherein said composition comprises an effective amount of the compound of claim 1, or a pharmaceutically acceptable salt, prodrug, or metabolite thereof, or a solvate or hydrate of any of the foregoing.

37. The composition of claim 34, wherein said composition is suitable for parenteral, transdermal, mucosal, nasal, buccal, sublingual, or oral administration to a subject in need thereof.

38. A method for treating a disease or disorder, said method comprising administering to a subject in need thereof an effective amount of the compound of claim 1, or a pharmaceutically acceptable salt, prodrug, or metabolite thereof, or a solvate or hydrate of any of the foregoing, wherein said disease or disorder is selected from the group consisting of neoplastic disease and autoimmune disease.

39. The method of claim 38, wherein said disease or disorder is selected from the group consisting of solid tumor and blood tumor.

40. The method of claim 38, wherein said disease or disorder is selected from the group consisting of lung cancer, blood cancer, breast cancer with or without lung metastasis, colon cancer with or without liver metastasis, rheumatoid arthritis, ischemia-reperfusion injury, and immune response induced during transplant rejection.

41. The method of claim 38, further comprises administering to a subject in need thereof one or more additional therapeutics including radiotherapy, chemotherapy, cell therapy and pharmaceutically active agents.

42. The method of claim 41, said agent is a checkpoint inhibitor.

43. The method of claim 38, wherein the compound of claim 1 is a PAD inhibitor and said PAD inhibitor attenuates an activity of a protein arginine deiminase (PAD).

44. The method of claim 43, wherein said PAD is selected from the group consisting of PAD2 and PAD4.

45. The method of claim 43, wherein said PAD is PAD4.

46. The method of claim 43, wherein said activity is revealed by an effect on the formation of neutrophil extracellular traps (NETs).

* * * * *